(12) United States Patent
Oonuma et al.

(10) Patent No.: US 8,852,530 B2
(45) Date of Patent: Oct. 7, 2014

(54) AUTOMATED ANALYZER

(75) Inventors: Takehiko Oonuma, Oyama (JP);
Tomohiro Sugimura, Otawara (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 26 days.

(21) Appl. No.: 13/039,949

(22) Filed: Mar. 3, 2011

(65) Prior Publication Data

US 2011/0223061 A1 Sep. 15, 2011

(30) Foreign Application Priority Data

Mar. 5, 2010 (JP) ................................ 2010-049222

(51) Int. Cl.
*G01N 1/10* (2006.01)
*G01N 35/10* (2006.01)

(52) U.S. Cl.
CPC ............ *G01N 35/10* (2013.01); *G01N 35/1004* (2013.01); *G01N 2035/1025* (2013.01); *G01N 35/1011* (2013.01)
USPC .............. 422/517; 422/519; 422/63; 436/180

(58) Field of Classification Search
CPC ............... G01N 2035/1011; G01N 2035/1025
See application file for complete search history.

(56) References Cited

U.S. PATENT DOCUMENTS

2005/0255005 A1* 11/2005 Motadel .................. 422/100

FOREIGN PATENT DOCUMENTS

| CN | 101310188 A | 11/2008 |
|---|---|---|
| JP | 2-77652 | 3/1990 |
| JP | 6-249862 | 9/1994 |
| JP | 2000-171470 | 6/2000 |
| JP | 2000-221201 | 8/2000 |
| JP | 2000-266765 | 9/2000 |
| JP | 2003-344426 | 12/2003 |
| JP | 2007-132855 | 5/2007 |
| JP | 2009-42067 | 2/2009 |
| JP | 2009180605 | * 8/2009 |

OTHER PUBLICATIONS

Chinese Office Action issued Dec. 3, 2012, in Chinese Patent Application No. 201110053298.9.
Japanese Office Action issued on Aug. 13, 2013, in Japanese Patent Application No. 2010-049222 filed Mar. 5, 2010 (in Japanese language).

* cited by examiner

*Primary Examiner* — P. Kathryn Wright
(74) *Attorney, Agent, or Firm* — Oblon, Spivak, McClelland, Maier & Neustadt, L.L.P.

(57) ABSTRACT

An automated analyzer according to an embodiment includes a probe. The probe has a step part configured to be provided between a lower shaft and an upper shaft, and to be formed such that the outer diameter changes. A descending controller lowers the probe from a predefined position that positions the step part above the liquid surface to an operating position that positions the step part below the liquid surface. A ascending controller raises the probe at a high speed from the operating position until immediately before the step part reaches the position of the liquid surface, subsequently raises the probe at a low speed until the step part passes through the liquid surface, and raises the probe at a higher speed than the low speed from immediately after the step part passes through the position of the liquid surface up to the predefined position.

3 Claims, 19 Drawing Sheets

FIG.4C

42
STORAGE PART

421

| t11 | t13 | t14 |
|-----|-----|-----|
| 0.4 | 0.4 | 0.9 |
| 0.5 | 0.3 | 0.8 |
| ⋮ | ⋮ | ⋮ |

422

| t21 | t23 | t24 |
|-----|-----|-----|
| 0.4 | 0.4 | 0.9 |
| 0.5 | 0.3 | 0.8 |
| ⋮ | ⋮ | ⋮ |

AUTOMATED ANALYZER

CROSS-REFERENCE TO RELATED APPLICATION

This application is based upon and claims the benefit of priority from Japanese Patent Application No. 2010-49222, filed Mar. 5, 2010; the entire contents of which are incorporated herein by reference.

FIELD

The embodiments of the present invention relate to an automated analyzer for samples and reagent.

BACKGROUND

Blood is constituted from blood cell components and plasma components. Blood cell components include red blood cells, white blood cells, and blood platelets.

A combination of hemoglobin in the red blood cells and blood glucose is known as glycohemoglobin. The more sugar that remains in the blood, the more glycohemoglobin is correspondingly obtained.

One example of glycohemoglobin is HbA1c. The measured value of HbA1c correlates with the mean value of the blood-sugar level for approximately the past 60 days from the time of blood collection. Based on that, it is possible to understand the blood condition of a subject for this period.

The collected blood is placed in a container and a rotor is put in place, with the bottom of the container facing out. When the container is rotated, a high gravity is applied to the blood, and the blood cell parts with greater specific gravity sink to the bottom.

Based on that, the plasma components are separated as a supernatant (centrifugation). Moreover, even without centrifugation, when the collected blood is placed in a container, the blood cell parts with greater specific gravity sink to the bottom.

Generally, when dispensing a serum, a probe is shallowly inserted into a container, the serum is absorbed by a specified amount only, and the absorbed serum is dispensed into a reaction container.

On the other hand, when dispensing the red blood cells that sink to the bottom of the container, it is necessary to insert the probe into the container deep and to absorb the red blood cells that have sunk on the bottom of the container.

With regard to the automated analyzer, in order to improve the accuracy of the dispensing, there is a probe in which the internal diameter and the outer diameter of the tip is formed so as to be as small as possible, and in which the overall length of the probe is supplemented from the tip to the upper side. Based on this, a step part is formed on the probe.

When performing an operation to absorb a sample that contains the red blood cells that have sunk to the bottom of the container, lower the step part of the probe from a predefined position above the liquid level of the sample inside the container to an operating position below the liquid level of the sample. After absorbing the red blood cells, raise the probe from the operating position to the predefined position. Subsequently, rotate the raised probe to the position of the reaction container and dispense the absorbed red blood cells into the reaction container.

When raising the probe from the operating position to the predefined position, the sample is attached to the step part of the probe that passes through the liquid level of the sample.

Subsequently, when rotating the raised probe to the position of the reaction container, the sample that is attached to the step part spatters and contaminates the surroundings. Moreover, there are cases in which the spattered sample enters the reaction container and causes a measurement error.

After absorbing the red blood cells, wash the outer side of the probe before dispensing into a reaction tube, and wash the inner side and the outer side of the probe after dispensing. With regard to the washing operation of the probe, lower the step part of the probe from the predefined position above the liquid level of the cleaning solution in the cleaning tank to the operating position below the liquid level of the cleaning solution. Based on that, it becomes possible to clean the outer diameter part of the probe, including the step part.

Moreover, by ejecting the water inside the probe from the tip of the probe, clean the internal diameter part. After cleaning the outer diameter part and the internal diameter part of the probe, raise the probe from the operating position to the predefined position.

Rotate the raised probe to a standby position and prepare for the subsequent dispensing of the sample.

When raising the probe from the operating position to the predefined position, cleaning water is attached to the step part of the probe that passes through the liquid level of the cleaning solution.

Subsequently, when rotating the raised probe to the standby position, the cleaning water that is attached to the step part spatters and contaminates the surroundings. Moreover, after cleaning the outer diameter part and the internal diameter part of the probe, when performing the subsequent dispensing of the sample, the cleaning water that is attached to the step part is brought inside the container, and the sample is diluted. This causes the measurement error in the constituent amount of reaction solution.

In order to cause the sample or the cleaning solution to be less likely to be attached to the step part of the probe, a phenomenon in which a sample or water that is attached to the probe side moves to the liquid level side due to surface tension can be used. In order to use this phenomenon, when raising the probe from the operating position to the predefined position, a method for raising the probe at a low speed can be considered. However, there are facts in which in order to perform a series of actions of automatic analysis in a cycle of, for example, 4.5 seconds, the probe cannot be raised across all sections from the operating position to the predefined position at the low speed.

There is a technology in which, in order to remove the cleaning water that is attached to the probe, a gas is spurted on the probe. Moreover, there is a technology that vacuum-absorbs the cleaning water that is attached to the probe. As a technology that spurts the gas on the probe, there is a technology that is set up above the movement path of the probe, that spurts gas from both sides on the probe in motion, and that dries the probe. The conventional technology, in which a gas 2 is spurted from both sides against a probe 1, is described with reference to FIG. 20. The gas 2 is sent to a nozzle 4 via a gas tube 3. A pathway through which the probe 1 passes is provided in a holding block 5. On the both walls of the pathway, the nozzle 4 is provided. On the road surface of the pathway, an outlet 6 is provided. Resulting from the gas 2 that is sprayed from the nozzle 4, the cleaning water that is attached to the probe 1 is blown off. The cleaning water that is blown off turns into a droplet 7 and flows into a drainpipe 8 from the outlet 6.

With regard to the probe having the step part, the conventional technology that processes the sample or cleaning solution that is attached to the step part has been described above;

however, regardless of the presence or absence of the step part, when pulling up a probe that is inserted deep into the sample, there are many cases in which the sample is attached to the tip part of the probe. The sample that is attached causes the spattering and contamination.

However, in order to remove the cleaning water that is attached to the probe, when using the technology that vacuum-absorbs the cleaning water that is attached to the probe, the structure of the cleaning tank turns complex. Moreover, in the technology in which the gas is spurted on the probe, although it depends on the ejection time and ejection amount, there is a problem in that drying the probe takes time.

Moreover, in order to reduce the amount of the sample that is attached to the tip part of the probe, the speed at which the probe is pulled up (ascending speed) may be set low. However, there were problems, in that raising the probe required a long time and in that the efficiency of the series of actions to dispense the sample decreased.

BRIEF DESCRIPTION OF THE DRAWINGS

FIG. 4C is a functional block diagram of a storage part.

DETAILED DESCRIPTION

[Structure]

Figure 1:
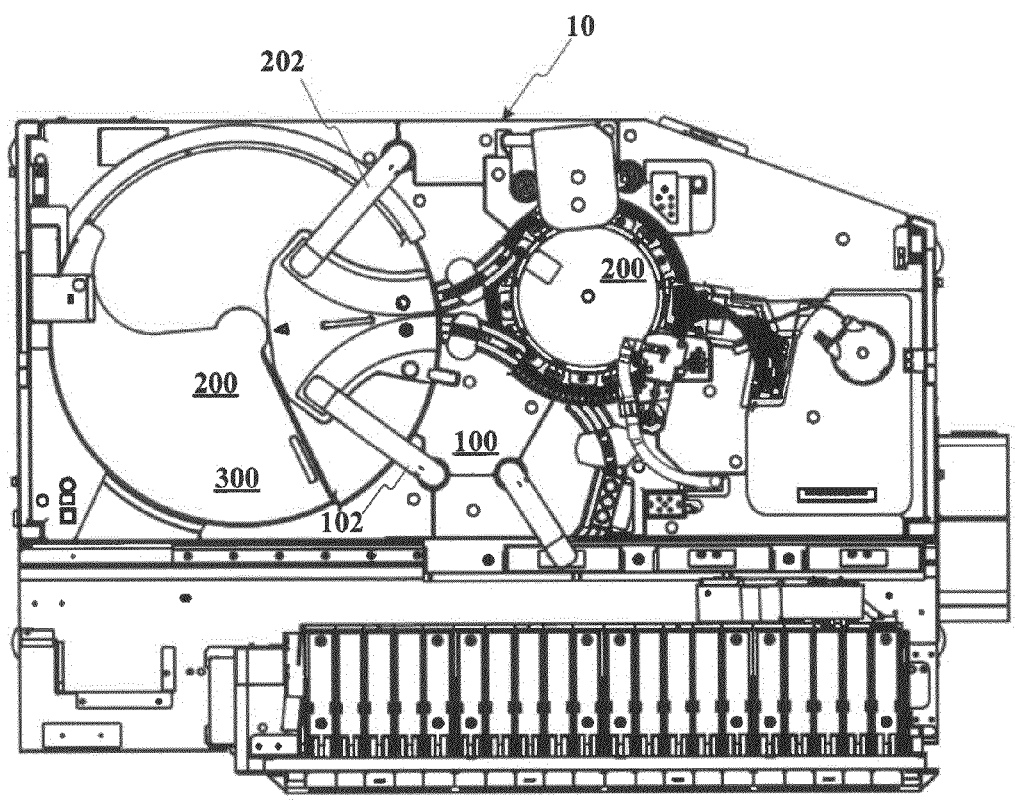
FIG. 1 is an overall view of an automated analyzer according to the first embodiment.

Below, various embodiments of the automated analyzer are described.

An automated analyzer according to an embodiment includes an axial probe. The probe is configured to move between below the liquid surface of any liquid among a sample, reagent, and cleaning water and above the liquid surface, dispense the sample and the reagent into a reaction container, and be cleaned with the cleaning water. The automated analyzer analyzes components of a reaction solution generated from the dispensed sample and reagent. The probe includes a step part configured to be provided between a lower shaft and an upper shaft, and to be formed such that the outer diameter changes. The automated analyzer includes a descending controller configured to lower the probe and an ascending controller configured to raise the probe. The descending controller is configured to lower the probe from a predefined position that positions the step part above the position of the liquid surface of the liquid to an operating position for performing absorption of the liquid or washing with the cleaning water by positioning the step part below the position of the liquid surface. The ascending controller is configured to raise the probe at a high speed from the operating position until immediately before the step part reaches the position of the liquid surface, subsequently raise the probe at a low speed that is lower than the high speed until the step part passes through the position of the liquid surface, and raise the probe at a higher speed than the low speed from immediately after the step part passes through the position of the liquid surface up to the predefined position.

Moreover, an automated analyzer according to another embodiment includes an axial probe configured to move between below the liquid surface of any liquid among a sample, reagent, and cleaning water and above the liquid surface, dispense the sample and the reagent into a reaction container, and be cleaned with the cleaning water. The automated analyzer analyzes components of a reaction solution generated from the dispensed sample and reagent.

The probe includes a step part configured to be provided between a lower shaft and an upper shaft, and to be formed such that the outer diameter changes. The automated analyzer includes a descending controller configured to lower the probe and an ascending controller configured to raise the probe. The descending controller is configured to lower the probe from a predefined position that positions the step part above the position of the liquid surface of the liquid to an operating position for performing absorption of the liquid or washing with the cleaning water by positioning the step part below the position of the liquid surface. The ascending controller is configured to raise the probe at a high speed from the operating position until immediately before the step part reaches the position of the liquid surface, and subsequently raise the probe at a low speed that is lower than the high speed up to the predefined position.

Furthermore, an automated analyzer according to another embodiment includes an axial probe configured to move between below the liquid surface of any liquid among a sample, reagent, and cleaning water and above the liquid surface, dispense the sample and the reagent into a reaction container, and be cleaned with the cleaning water. The automated analyzer analyzes components of a reaction solution generated from the dispensed sample and reagent.

The probe includes a step part configured to be provided between a lower shaft and an upper shaft, and to be formed such that the outer diameter changes. The automated analyzer includes a descending controller configured to lower the probe and an ascending controller configured to raise the probe. The descending controller is configured to lower the probe from a predefined position that positions the step part above the position of the liquid surface of the liquid to an operating position for performing absorption of the liquid or washing with the cleaning water by positioning the step part below the position of the liquid surface. The ascending controller is configured to raise the probe at a low speed from the operating position until the step part passes through the position of the liquid surface, and raise the probe at a higher speed than the low speed from immediately after the step part passes through the position of the liquid surface up to the predefined position.

Furthermore, an automated analyzer according to another embodiment includes an axial probe configured to move between below the liquid surface of any liquid among a sample, reagent, and cleaning water and above the liquid surface, dispense the sample and the reagent into a reaction container, and be cleaned with the cleaning water. The automated analyzer analyzes components of a reaction solution generated from the dispensed sample and reagent.

The probe includes a step part configured to be provided between a lower shaft and an upper shaft, and to be formed such that the outer diameter changes. The automated analyzer includes a descending controller configured to lower the probe and an ascending controller configured to raise the probe. The descending controller is configured to lower the probe from a predefined position that positions the lower end of the probe above the position of the liquid surface of the liquid to an operating position for performing absorption of the liquid or washing with the cleaning water by positioning the step part below the position of the liquid surface. The ascending controller is configured to, when raising the probe from the operating position to the predefined position, with respect to the speed in the section from the operating position until immediately before the step part reaches the position of the liquid surface, and with respect to the speed in the section from immediately after the lower end of the probe passes through the position of the liquid surface up to the predefined position, reduce, at least, the speed in the section from immediately before the step part reaches the position of the liquid surface until the step part passes through the position of the liquid surface, and the speed in the section from immediately before the lower end of the probe reaches the position of the liquid surface until the lower end passes through the position of the liquid surface.

Furthermore, an automated analyzer according to another embodiment includes an axial probe configured to move between below the liquid surface of any liquid among a sample, reagent, and cleaning water and above the liquid surface, dispense the sample and the reagent into a reaction container, and be cleaned with the cleaning water. The automated analyzer analyzes components of a reaction solution generated from the dispensed sample and reagent.

The automated analyzer includes a descending controller configured to lower the probe and an ascending controller configured to raise the probe. The descending controller is configured to lower the probe from a predefined position that positions the lower end of the probe above the position of the liquid surface of the liquid to an operating position for performing absorption of the liquid or washing with the cleaning water by positioning the lower end below the position of the liquid surface. The ascending controller configured to raise the probe at a high speed from the operating position until immediately before the lower end reaches the position of the liquid surface, subsequently raise the probe at a low speed that is lower than the high speed until the lower end passes through the position of the liquid surface, and raise the probe at a higher speed than the low speed from immediately after the lower end passes through the position of the liquid surface up to the predefined position.

Furthermore, an automated analyzer according to another embodiment includes an axial probe configured to move between below the liquid surface of any liquid among a sample, reagent, and cleaning water and above the liquid surface, dispense the sample and the reagent into a reaction container, and be cleaned with the cleaning water. The automated analyzer analyzes components of a reaction solution generated from the dispensed sample and reagent.

The automated analyzer includes a descending controller configured to lower the probe and an ascending controller configured to raise the probe. The descending controller is configured to lower the probe from a predefined position that positions the lower end of the probe above the position of the liquid surface of the liquid to an operating position for performing absorption of the liquid or washing with the cleaning water by positioning the lower end below the position of the liquid surface. The ascending controller is configured to raise the probe at a high speed from the operating position until immediately before the lower end reaches the position of the liquid surface, and subsequently raise the probe at a low speed that is lower than the high speed up to the predefined position.

Furthermore, an automated analyzer according to another embodiment includes an axial probe configured to move between below the liquid surface of any liquid among a sample, reagent, and cleaning water and above the liquid surface, dispense the sample and the reagent into a reaction container, and be cleaned with the cleaning water. The automated analyzer analyzes components of a reaction solution generated from the dispensed sample and reagent.

The automated analyzer includes a descending controller configured to lower the probe and an ascending controller configured to raise the probe. The descending controller is configured to lower the probe from a predefined position that positions the lower end of the probe above the position of the liquid surface of the liquid to an operating position for performing absorption of the liquid or washing with the cleaning water by positioning the lower end below the position of the liquid surface. The ascending controller is configured to raise the probe at a low speed from the operating position until the lower end passes through the position of the liquid surface, and raise the probe at a higher speed than the low speed from immediately after the lower end passes through the position of the liquid surface up to the predefined position.

First Embodiment

Figure 2:
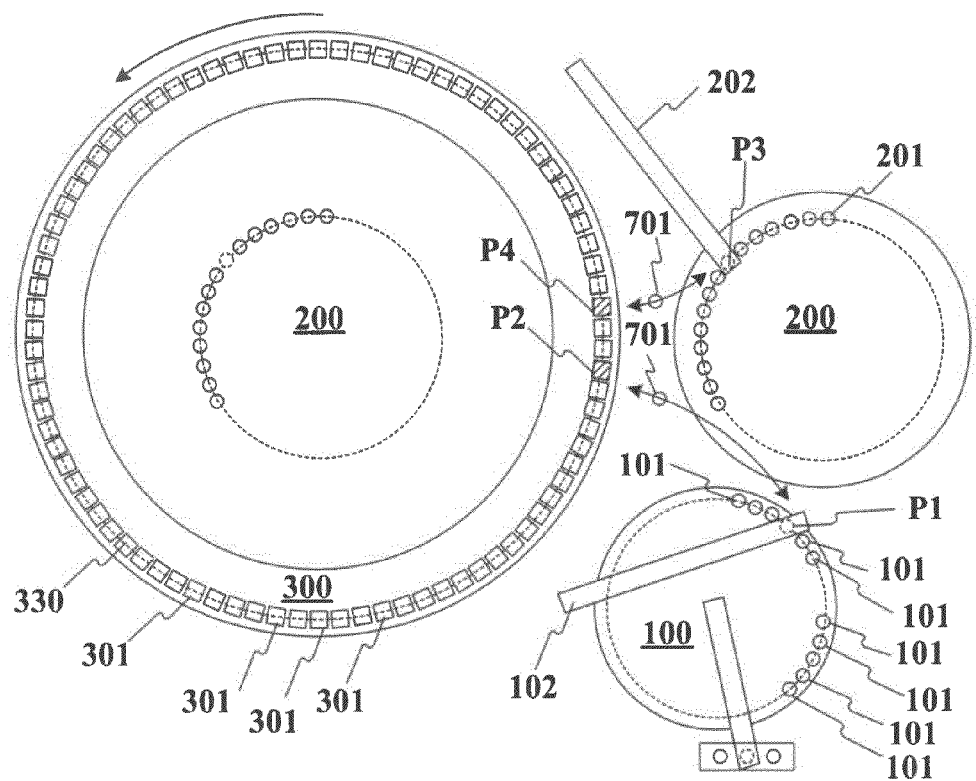
FIG. 2 is a conceptual view of the automated analyzer.
Figure 3:
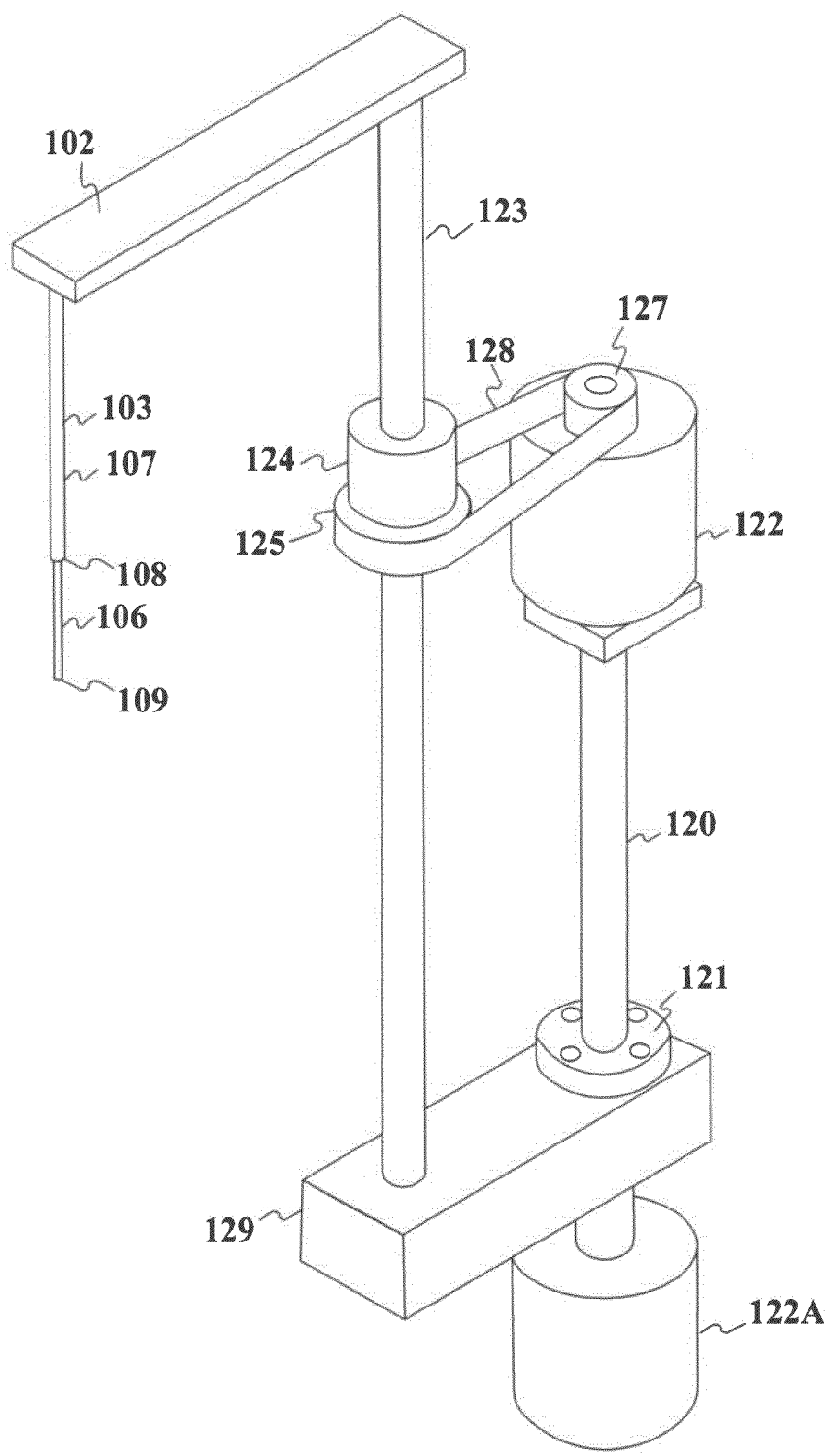
FIG. 3 is a perspective view of a sample probe, a sample arm, and a sample-probe driver.
Figure 4A:
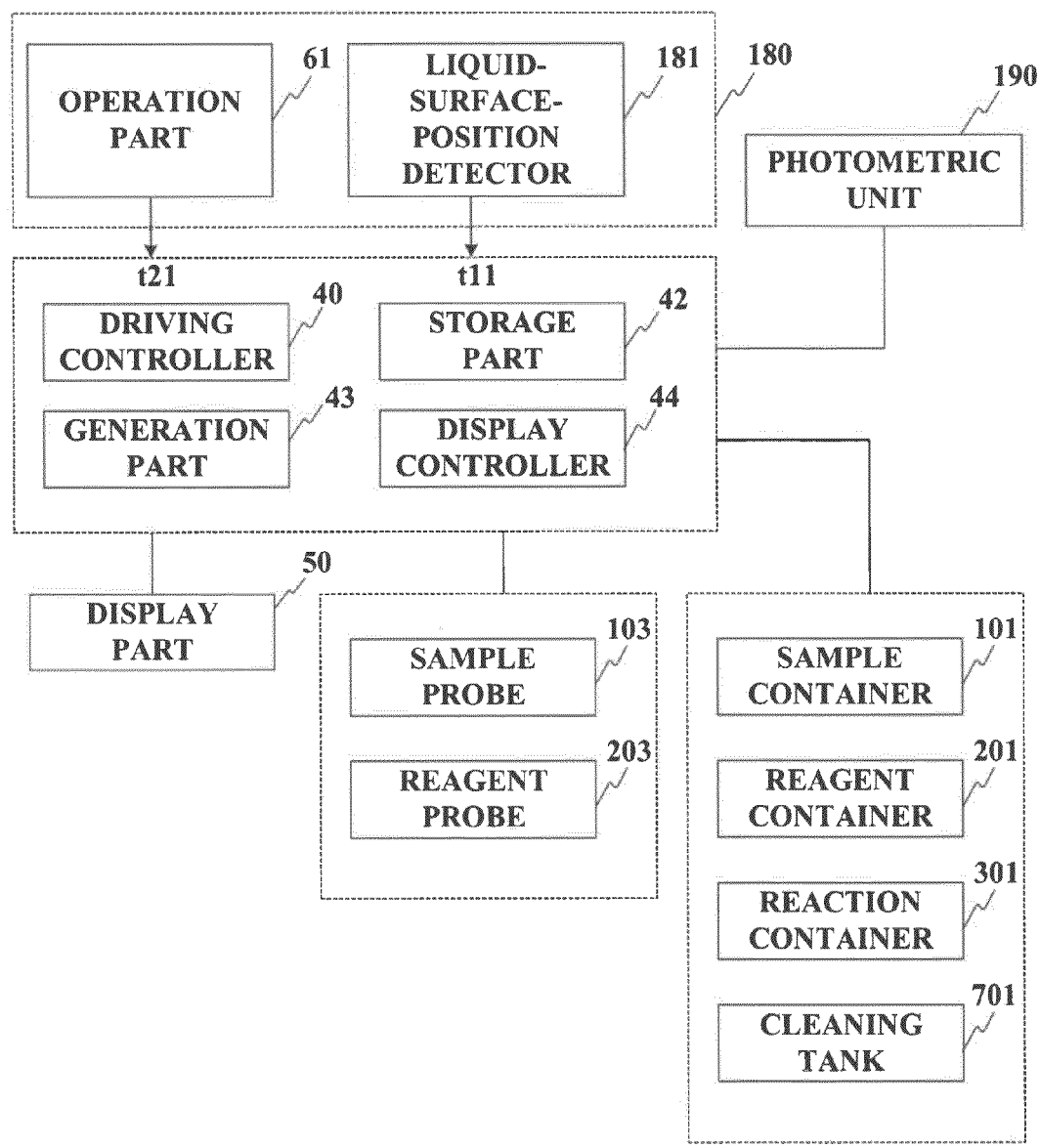
FIG. 4A is a functional block diagram of the automated analyzer.

An embodiment according to an automated analyzer is described below with reference to FIG. 1-FIG. 10. FIG. 1 is an overall view of an automated analyzer. FIG. 2 is a conceptual view of an automated analyzer. FIG. 3 is a perspective view of a sample probe, a sample arm, and a driving device. FIG. 4A is a functional block diagram of the automated analyzer.

First, the basic structure of an automated analyzer is described with reference to FIG. 1, FIG. 2, and FIG. 4A. An automated analyzer 10 comprises a sample storage 100, sample containers 101 that house a sample (biological sample), a sample arm 102, a sample probe 103, first and second reagent storage 200, a reagent containers 201 that house a reagent, a reagent arm 202, a reagent probe 203, a reaction storage 300, reaction containers 301, a driving controller 40, a storage part 42, a generation part 43, a display controller 44, a display part 50, a cleaning tank 701, a pump for absorbing and discharging a sample (omitted in the figures), a solenoid valve (omitted in the figures), and an actuator for driving the solenoid valve (omitted in the figures).

The pump has a stepping motor. The stepping motor changes the absorption speed and the discharge speed of a sample, etc., depending on its rotation speed. By changing the rotation speed or rotation time of the stepping motor, it is possible to change the absorption amount and discharge amount of a sample, etc.

Figure 4B:
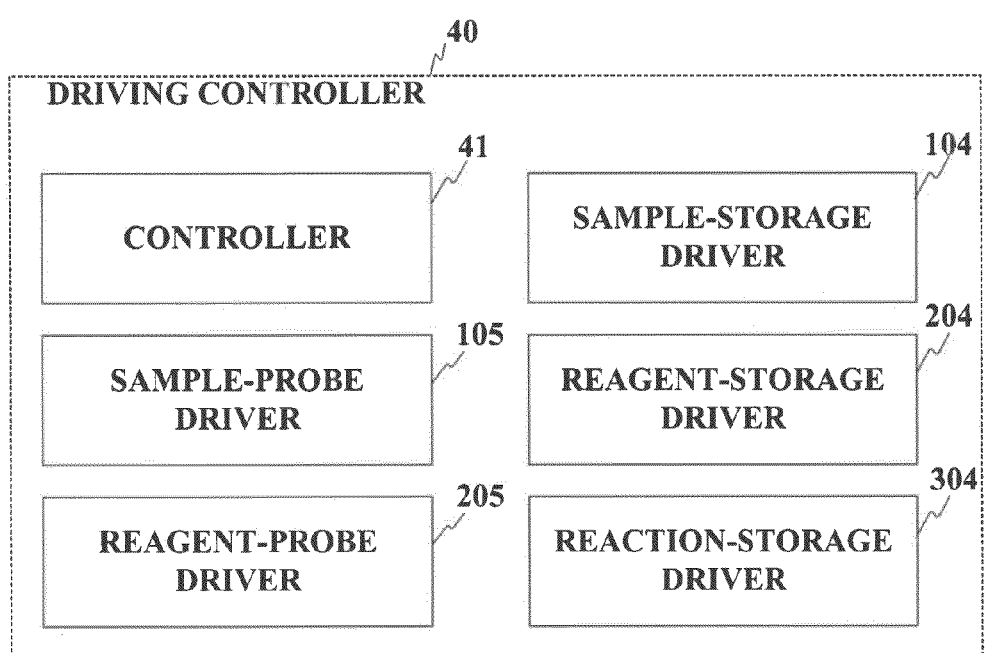
FIG. 4B is a functional block diagram of a driving controller.

FIG. 4B is a functional block diagram of a driving controller 40. As shown in FIG. 4B, the driving controller 40 includes a controller 41. Moreover, the driving controller 40 includes a sample-storage driver 104, a sample-probe driver 105, a reagent-storage driver 204, a reagent-probe driver 205, and a reaction-storage driver 304. These driving parts operate respectively upon receiving a command from the controller 41.

The controller 41 controls various driving parts including the sample-storage driver 104, the sample-probe driver 105, the reagent-storage driver 204, the reagent-probe driver 205, the reaction-storage driver 304 the pump described above, the solenoid valve described above, and the actuator described above.

The controller 41 causes the storage part 42 to store control information for controlling the various driving parts. The generation part 43 generates the control information that should be stored in the storage part 42 upon receiving a command from the controller 41.

The controller 41 reads out the control information from the storage part 42 and controls the sample-probe driver 105, etc. The controller 41 comprises a descending controller that controls the descending action and an ascending controller that controls the ascending action of the sample probe 103.

Next, the sample storage 100 and the sample-probe driver 105, representing the various driving parts described above, are described with reference to FIG. 1 to FIG. 3.

The sample storage 100 comprises a sample rack 130 and the sample-storage driver 104. The sample rack 130 is a disk sampler on which the plurality of sample containers 101 is mounted in a circumferential direction. The sample-storage driver 104, by rotating the sample rack 130 in a circumferential direction, transports the plurality of sample containers 101 sequentially to the absorption position.

On the tip part of the sample arm 102, the sample probe 103 is provided. The sample probe 103 is formed in an axial shape. The sample probe 103 comprises a lower shaft 106 in which the outer diameter is formed so as to be small, and an upper shaft 107 in which the outer diameter is formed so as to be large. Between the lower shaft 106 and the upper shaft 107, a step part 108 that is formed such that the size of the outer diameter changes is provided. The lower shaft 106 refers to the area from the bottom of the step part 108 up to the lower end 109. By forming the outer diameter of the lower shaft 106 so as to be small, it is possible to absorb the minimum amount of the sample. Moreover, by fitting the upper shaft 107 having the large outer diameter to the lower shaft 106, it is possible to improve the overall strength of the sample probe 103. Although the sample probe in which the diameter of the outer shape of the step part 108 is reduced to be nearly perpendicular has been shown in FIG. 3, the outer shape of the step part 108 is not limited to this, and for example, it may be taper-shaped.

It is preferable that the step part 108 is coated with a fluororesin. As the fluororesin, the fluororesin with the excellent water repellency is preferable, and further, the fluororesin with a large contact angle is preferable. Such fluororesin, for example, includes PTFE (polytetrafluoroethylene), FEP (fluorinated ethylene-propylene: ethylene tetrafluoride-propylene hexafluoride copolymer), and PFA (perfluoroalkoxy: ethylene tetrafluoride perfluoro propyl vinyl ether), etc.

A stepping motor 122 rotates the sample probe 103 between the absorption position P1 and the discharge position P2. The sample probe 103 that is rotated to the absorption position P1 absorbs the sample from the sample containers 101 that are transported to the absorption position P1. The sample probe 103 that is rotated to the discharge position P2 discharges the absorbed sample to the reaction containers 301 that are transported to the discharge position P2. The stepping motor 122 moves the sample probe 103 to the cleaning position and the standby position.

On the tip of the sample arm 102, the sample probe 103 is fixed perpendicular to the axial direction. The tail end of the sample arm 102 is fixed and supported to the upper end of a spline axis 123 that is provided perpendicular to the axial direction. In the nearly middle of the spline axis 123, a rotating mechanism 124 is fixed. To the rotating mechanism 124, a spline-side pulley 125 is provided concentrically. A motor-side pulley 127 is fixed to the frame of the automated analyzer 10 (omitted in the figures), and is fixed to the rotating shaft of the stepping motor 122 constituting the drive source of the rotating mechanism 124. Between the spline-side pulley 125 and the motor-side pulley 127, a rotating belt 128 is bridged over.

Based on this, the spline-side pulley 125 synchronizes and rotates with respect to the rotation of the motor-side pulley 127. In this way, the stepping motor 122 rotates the sample probe 103 centering around the spline axis 123 between the absorption position P1 (position of the sample container 101) and the discharge position P2 (position of the reaction container 301).

Figure 5:
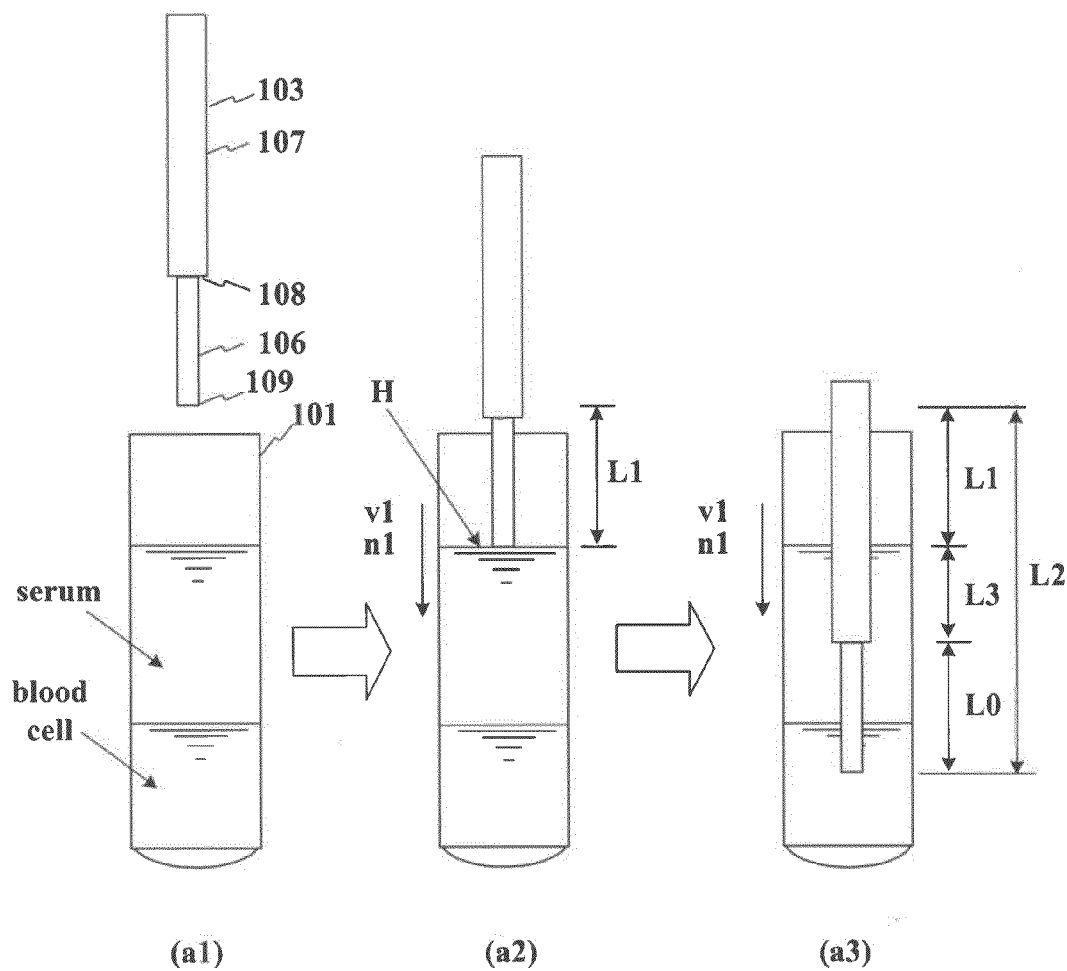
FIG. 5 is a diagram showing the action of a probe.
Figure 6:
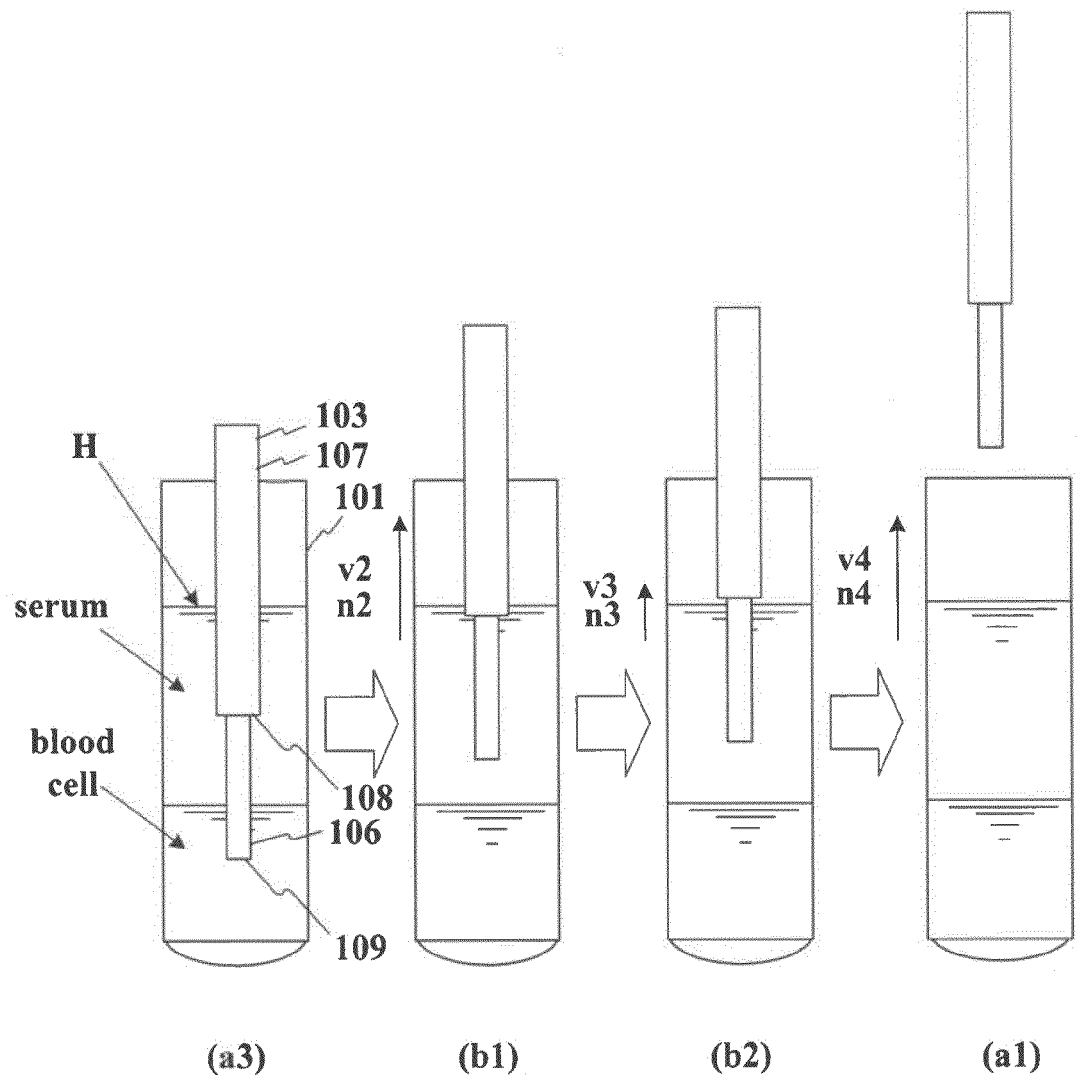
FIG. 6 is a diagram showing the moving speed of the probe when ascending.
Figure 7A:
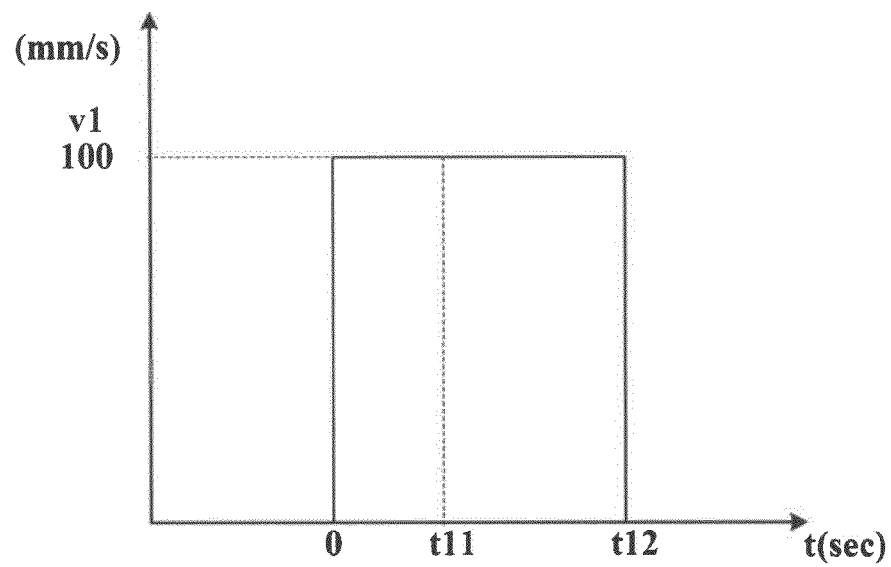
FIG. 7A is a velocity diagram of the probe when descending.
Figure 7B:
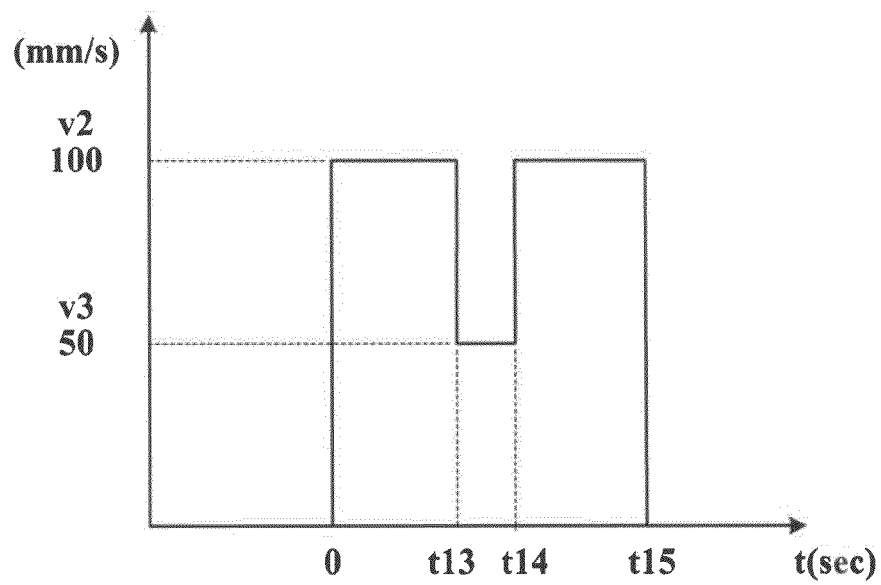
FIG. 7B is a velocity diagram of the probe when ascending.
Figure 8:
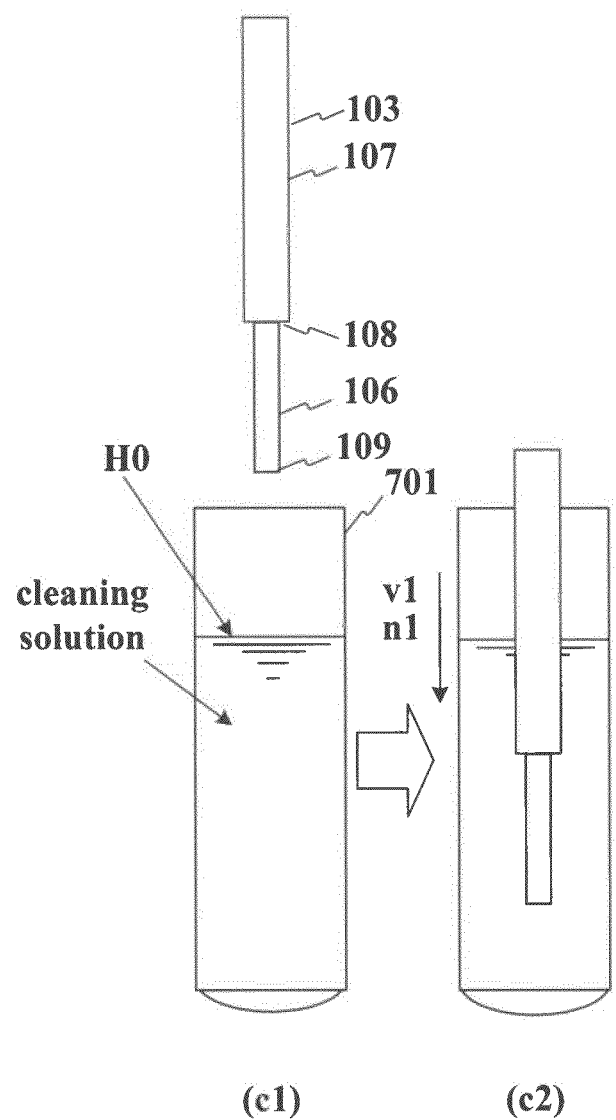
FIG. 8 is a diagram showing the moving speed of the probe when descending into a cleaning solution.

Next, the structure for controlling the sample-probe driver 105 is described with reference to FIG. 3-FIG. 8. FIG. 4C is a functional block diagram of a storage part. FIG. 5 is a diagram showing the respective action of a sample probe. FIG. 6 is a diagram showing the moving speed of a sample probe when ascending. FIG. 7A is a velocity diagram of the sample probe when descending. FIG. 7B is a velocity diagram of the sample probe when ascending. FIG. 8 is a diagram showing the moving speed of the probe when descending into the cleaning solution. Moreover, below, primarily, the control structure of the sample-probe driver 105 in cases in which the liquid is attached to the step part 108 of the sample probe 103 is described.

However, in the embodiment, the reagent probe 203 may be the control subject. Moreover, when the liquid (including a sample, reagent, and cleaning water) is attached to the step part 108 and the lower end 109 of the sample probe 103 (including the step part and the lower end of the reagent probe 203), it may have the control structure of the sample-probe driver 105 or the reagent-probe driver 205 for cases in which the liquid is attached to the step part 108 and the lower end 109. Moreover, cases in which the liquid is attached to the step part 108 and the lower end 109 are described subsequently.

Moreover, when the amount of the liquid that is attached to the step part 108 is extremely small and when it does not result in a measurement error, it may have the control structure of the sample-probe driver 105 or the reagent-probe driver 205 when the liquid is attached to the lower end 109 only. Cases in which the liquid is attached to the lower end 109 only are also described subsequently.

Below, the control structure of the sample probe 103 in cases in which the liquid is attached to the step part 108 of the sample probe 103 only is described.

First, the structure for controlling the sample-probe driver 105 when dispensing the sample is described.

The controller 41, when dispensing the sample by descending and ascending the sample probe 103, causes the storage part 42 to store the respective time required for the sample probe 103 to reach the respective position of a predefined positional, a liquid level detecting position a2, an operating position a3, a position immediately before passing through the liquid level b1, and a position immediately after passing through the liquid level b2.

The above respective positions a1, a2, a3, b1, and b2 are shown in FIG. 5 and FIG. 6. Moreover, the position of the liquid level that is detected is shown as H in FIG. 5 and FIG. 6. Moreover, the information regarding the respective time required that is stored in the storage part 42 is shown in FIG. 4C as a part of control information 421. Moreover, in FIG. 7A, examples of the time required are shown as t11 and t12. Moreover, in FIG. 7B, examples of the time required are shown as t13, t14, and t15.

Next, the display and the change of the control information 421 are described. The display controller 44 causes the display part 50 to display the control information including the default value. The controller 41, upon receiving a change command resulting from an operation by an operation part 61, causes the storage part 42 to store the changed control information, and at the same time, and causes the display controller 44 to display the changed control information.

Moreover, the controller 41 causes the generation part 43 to generate the control information, upon receiving detection signals from a liquid-surface-position detector 181. Furthermore, the controller 41 causes the storage part 42 to store the generated control information, and at the same time, causes the display controller 44 to display the generated control information. The operation part 61 and the liquid-surface-position detector 181 serve as a liquid-surface-information input part 180 for inputting the control information. The liquid-surface-position detector 181 is, for example, a liquid level sensor of capacitance type that detects the position of the liquid level by detecting an electric change when the sample probe 103 touches the liquid surface. The liquid-surface-position detector 181 may be an optical type or an ultrasonic type liquid level sensor. Here, the default value is the information that is previously defined and stored by associating with the patient information regarding patients who are the subjects of the measurement or by associating with measurement items. Moreover, there are cases in which the position of the liquid level of the liquid refers to both the position of the detected liquid surface and the position of the previously defined liquid level.

Here, the control of the controller 41 that operates the sample probe 103 based on the control information that is stored in the storage part 42, is described. The controller 41 generates a driving pulse based on the control information and outputs the generated driving pulse to the stepping motor 122 of the sample-probe driver 105. The stepping motor 122 rotates the sample probe 103 between the absorption position P1 and the discharge position P2 by rotating at a predefined speed by a predefined angle corresponding to the driving pulse.

The lower end of the spline axis 123 is supported rotatably by a block 129. A nut 121 for a ball screw 120 is fixed to the block 129.

Moreover, to the ball screw 120, a rotating shaft of a vertical-movement stepping motor 122A that is fixed to the frame of the automated analyzer 10 is directly linked. As the ball screw 120 rotates, the nut 121 moves vertically. Accordingly, the block 129 moves vertically. Based on that, the sample probe 103 is raised or lowered between the predefined position and the operating position.

The controller 41 generates a driving pulse based on the control information and outputs to the vertical-movement stepping motor 122A of the sample-probe driver 105. The controller 41 provides the number of pulse per unit time (for 1 second) (hereinafter referred to as simply "pulse number") to the vertical-movement stepping motor 122A. The vertical-movement stepping motor 122A rotates at a rotation speed that is the value that multiplies the step angle by the pulse number. The controller 41 increases or reduces the rotation speed of the vertical-movement stepping motor 122A by increasing or reducing the pulse number provided to the vertical-movement stepping motor 122A. Based on that, the sample probe 103 is raised or lowered at predefined speed.

Next, the controller 41 controls the action of the sample probe 103 based on the control information 421 that is stored in the storage part 42.

First, the relationship between the speed of the sample probe 103 and the pulse number provided to the vertical-movement stepping motor 122A is described. When the step angle is set to be θ and the pulse number is set to be n, the speed v of the sample probe 103 is expressed in the following formula (1).

$$v = \gamma \cdot \theta \cdot n \quad (1)$$

wherein, γ is the amount (feed) at which the nut 121 is moved relatively to the ball screw 120 when the vertical-movement stepping motor 122A is rotated by the step angle (θ).

As described above, the nut 121 is constituted so as to move in a vertical direction along with the block 129, the spline axis 123, the sample arm 102, and the sample probe 103. Therefore, the speed at which the nut 121 is moved is equivalent to the speed at which the sample probe 103 is moved in a vertical direction. Moreover, as clear from the above formula (1), the pulse number that is provided to the vertical-movement stepping motor 122A is proportional to the speed at which the sample probe 103 is moved in a vertical direction.

Next, an explanation is provided regarding the relationship between the pulse number n that is provided to the vertical-movement stepping motor 122A, the amount of time required t for the movement, and the distance L by which the sample probe 103 is moved during the required time t, in order for the controller 41 to move the sample probe 103 at the speed v. The relationship between the pulse number n, the amount of time required t, and the distance L can be expressed in the following relational expression (2).

$$n = L/(\gamma \cdot \theta \cdot t) \quad (2)$$

Using the above formula (2), the generation part 43 can calculate the distance L, based on the amount of time required t that is calculated and the previously defined pulse number n. Based on the amount of time required t that is stored in the storage part 42 and the previously defined or previously calculated distance L, the pulse number n can be obtained. Moreover, the generation part 43 can calculate the amount of time required t, based on the previously defined pulse number n and the previously defined or previously calculated L.

For example, the generation part 43 can calculate the distance L1 (=n1·γ·θ·t11) using the above formula (2), wherein t11 refers to the time required from the time when the sample probe 103 descends from the predefined position until the liquid-surface-position detector 181 detects the liquid level, and n1 refers to the predefined pulse number that is proportional to the speed v1 at which the sample probe 103 descends.

Next, the generation of the control information 421 is described with reference to FIG. 5 to FIG. 7B. The generation part 43 generates the control information 421 according to a command from the controller 41, based on the detected information from the liquid-surface-position detector 181. Moreover, when lowering the sample probe 103, the speed in the section from the predefined position to the operating position, and the speed at which the sample probe 103 is raised (the respective speed in the section from the operating position up to the position immediately before passing through, the section from the position immediately before passing through up to the position immediately after passing through, and the section from the position immediately after passing through up to the predefined position) are not constant. For example, at the boundary of the respective section, after accelerating or slowing down, a fixed speed is retained, and subsequently, it slows down or accelerates. Here, for explanation purposes, the speed in the respective section is referred to as the mean speed in the respective section. The mean speed in the respective section is shown in FIG. 7A and FIG. 7B.

In order to absorb the blood cells that sank on the bottom of the sample container 101, the controller 41 provides the previously defined pulse number n1 to the vertical-movement stepping motor 122A. Based on that, the controller 41 lowers the sample probe 103 from the predefined position to the operating position. Moreover, upon receiving an operation from the operation part 61, the controller 41 causes the storage part 42 to store the amount of time required t12 for the sample probe 103 from starting descending until the completion of descent (when it reaches the operating position).

While the sample probe 103 is descending, the liquid-surface-position detector 181 detects that the sample probe 103 touched the liquid surface and outputs the liquid level detection signals to the controller 41. The controller 41 outputs the amount of time required t11 for the sample probe 103 from starting descending until it receives the liquid level detection signals t11 to the generation part 43. Upon receiving the required time t11, the generation part 43 calculates the distance L1 ($=n1 \cdot \gamma \cdot \theta \cdot t11$) based on the above formula (2).

The controller 41 completes providing the pulse number n1 to the vertical-movement stepping motor 122A and stops the sample probe 103 from descending. The generation part 43 calculates the distance L2 ($=n1 \cdot \gamma \cdot \theta \cdot t12$), based on the amount of time required t12 for the sample probe 103 from starting descending until the completion of descent and based on the previously defined pulse number n1.

The generation part 43 subtracts the distance L1 ($=n1 \cdot \gamma \cdot \theta \cdot t11$) from the distance L2 ($=n1 \cdot \gamma \cdot \theta \cdot t12$). Moreover, the generation part 43 subtracts the length of the lower shaft 106, that is, the distance L0 from the tip of the sample probe 103 to the step part 108, from the difference between the distance L2 and the distance L1.

Based on that, the generation part 43 calculates the distance L3 ($=n1 \cdot \gamma \theta(t12-t11)-L0$) from the step part 108 to the position of the liquid surface.

The process in which the generation part 43 calculates the distance L1, the distance L2, and the distance L3 from the pulse number n1, and the amount of time required t11 and t12 has been described above.

A phase (a1) in FIG. 5 (the sample probe 103 is located at the above-mentioned positional) shows the blood cells that sank on the bottom of the sample container 101 and the blood plasma as the supernatant. A phase (a2) in FIG. 5 (the sample probe 103 is located at the above-mentioned position a2) shows the sample probe 103 when the step part 108 touches the liquid surface. A phase (a3) in FIG. 5 (the sample probe 103 is located at the above-mentioned position a3) shows the sample probe 103 when the step part 108 is moved below the liquid surface and reaches to operating position, in order to absorb the blood cells that sank on the bottom of the sample container 101. Moreover, FIG. 7A shows the amount of time required t11 for the sample probe 103 from starting descending until the liquid level detection signal is received, and the previously defined required time t12 for the sample probe 103 from starting descending until the completion of descent (when it reaches the operating position).

Next, an example of the method for the generation part 43 to calculate the time required for the sample probe 103 from starting ascending until it passes through the liquid surface is described.

After absorbing the blood cells that sank on the bottom of the sample container 101, in order to raise the sample probe 103 from the operating position to the predefined position, the controller 41 provides the previously defined pulse number n2 to the vertical-movement stepping motor 122A. Based on that, the sample probe 103 is raised from the operating position to the predefined position.

While the sample probe 103 is being raised by the distance L3 that is calculated by the generation part 43, the step part 108 of the sample probe 103 passes through the liquid surface.

Based on the above formula (2), the generation part 43 calculates the time required t10 for the sample probe 103 from starting ascending until the step part 108 passes through the liquid surface.

$$t10 = L3/(n2 \cdot \gamma \cdot \theta)$$

wherein the L3 is the distance expressed by ($n1 \cdot \gamma \cdot \theta(t12-t11)-L0$).

Moreover, the n2 is the pulse number.

The generation part 43 subtracts the previously defined time t3 from the calculated time required t10, and calculates the time required t13 for the sample probe 103 from starting ascending until immediately before the step part 108 passes through the liquid surface. Moreover, the generation part 43 calculates the time required t14 for the sample probe 103 from starting ascending until immediately after the step part 108 passes through the liquid surface, by adding the previously defined time t4 to the time required t10.

The method for calculating the time required t10 for the sample probe 103 from starting ascending until the step part 108 passes through the liquid surface has been described. Moreover, the method for calculating the time required t13 for the sample probe 103 from starting ascending until immediately before the step part 108 passes through the liquid surface has been described. Furthermore, the method for calculating the time required t14 for the sample probe 103 from starting ascending until immediately after the step part 108 passes through the liquid surface has been described. Moreover, upon receiving an operation from the operation part 61, the controller 41 causes the storage part 42 to store the time required t15 for the sample probe 103 from starting ascending until it completes ascending (when it reaches the predefined position).

The controller 41 starts or completes providing the predefined pulse number to the vertical-movement stepping motor 122A, based on the time required t13 and t14 that are calculated according to the above, and the required time t15 that is previously defined.

For example, the controller 41 provides the pulse number n2 to the vertical-movement stepping motor 122A and raises the sample probe 103 from the operating position at a high speed v2 ($=n2 \cdot \gamma \cdot \theta$).

Upon receiving the time required t13 from the start of ascent, the controller 41 provides the pulse number n3 to the vertical-movement stepping motor 122A and from immediately before the step part 108 passes through the position of the liquid surface, it raises the sample probe 103 at a low speed v3 (=n3·γ·θ). Upon receiving the time required t14 from the start of ascent, the controller 41 provides the pulse number n4 to the vertical-movement stepping motor 122A and from immediately after the step part 108 passes through the position of the liquid surface, it raises the sample probe 103 at a high speed v4 (=n4·γ·θ). Upon receiving the time required t15 from the start of ascent, the controller 41 completes provision of the pulse number to the vertical-movement stepping motor 122A, and stops raising the sample probe 103.

As above, because the sample probe 103 is raised at the low speed v3 between the time required t13 and the time required t14, and because the step part 108 of the sample probe 103 passes through the liquid surface in this period, it is possible to cause the liquid (blood plasma) to be less likely to be attached to the step part 108.

In order to cause the liquid (blood plasma) to be less likely to be attached, the low speed v3, for example, can be set to be the half the high speed v2. Furthermore, the low speed v3 can be set to be 50 mm/sec or less. Upon receiving the operation from the operation part 61, the controller 41 causes the storage part 42 to store by setting the v3 to be 50 mm/sec, and the high speed v2 and v4 to be 100 mm/sec.

The controller 41 provides the pulse numbers n2, n3, and n4 corresponding to the high speed v2, the low speed v3, and the high speed v4, respectively, to the vertical-movement stepping motor 122A. Moreover, the high speed v2 and the v4 may not have to be equal.

Moreover, upon receiving the operation from the operation part 61, the controller 41 adjusts the low speed v3, and the high speed v2 and v4 within the previously defined range. Moreover, the controller 41 causes the storage part 42 to store the adjusted high speed v2, the low speed v3, and the high speed v4.

The structure for controlling the sample-probe driver 105 when dispensing the sample has been described above.

Next, the structure for controlling the sample-probe driver 105 when cleaning the sample probe 103 after dispensing the sample is described. The structure when cleaning the sample probe 103 is basically the same as the structure described above regarding the cases in which the sample probe 103 is dispensed. The structure that is the same between both cases, for example, the structure in which the controller 41 provides the pulse number to the sample-probe driver 105 and in which it raises the sample probe 103, has been omitted, and the structure that is different between both cases is primarily described.

When cleaning the sample probe 103, the sample probe 103 is moved to the predefined position of the cleaning tank 701 that is filled with the cleaning water. The controller 41, by providing the pulse number to the vertical-movement stepping motor 122A, based on the control information 422 including the default value, lowers the sample probe 103 to the operating position at which the step part 108 of the sample probe 103 is placed below the liquid surface of the cleaning water. Here, the default value is the information that is previously defined and stored by associating with the patient information regarding patients who are the subjects of measurement or by associating with measurement items.

FIG. 4C shows a part of the control information 422.

Moreover, FIG. 8 shows the cleaning tank 701 that is filled with the cleaning water, and the sample probe 103 that is located at the predefined position, and the sample probe 103 that is lowered to the operating position.

In the structure for cleaning the sample probe 103, the controller 41, upon receiving the operation from the operation part 61, causes the storage part 42 to store the control information. The control information includes the time required t21 for the sample probe 103 from starting descending until it touches the liquid surface of the cleaning water. Because it is possible to calculate the position of the liquid surface based on the time required t2, the liquid-surface-position detector 181 for detecting the position of the liquid surface is no longer necessary. Here, the control information (required time) is shown as t2 in FIG. 4C. Moreover, the position of the liquid surface that is previously defined is shown as H0 in FIG. 8.

[Action]

Figure 9:
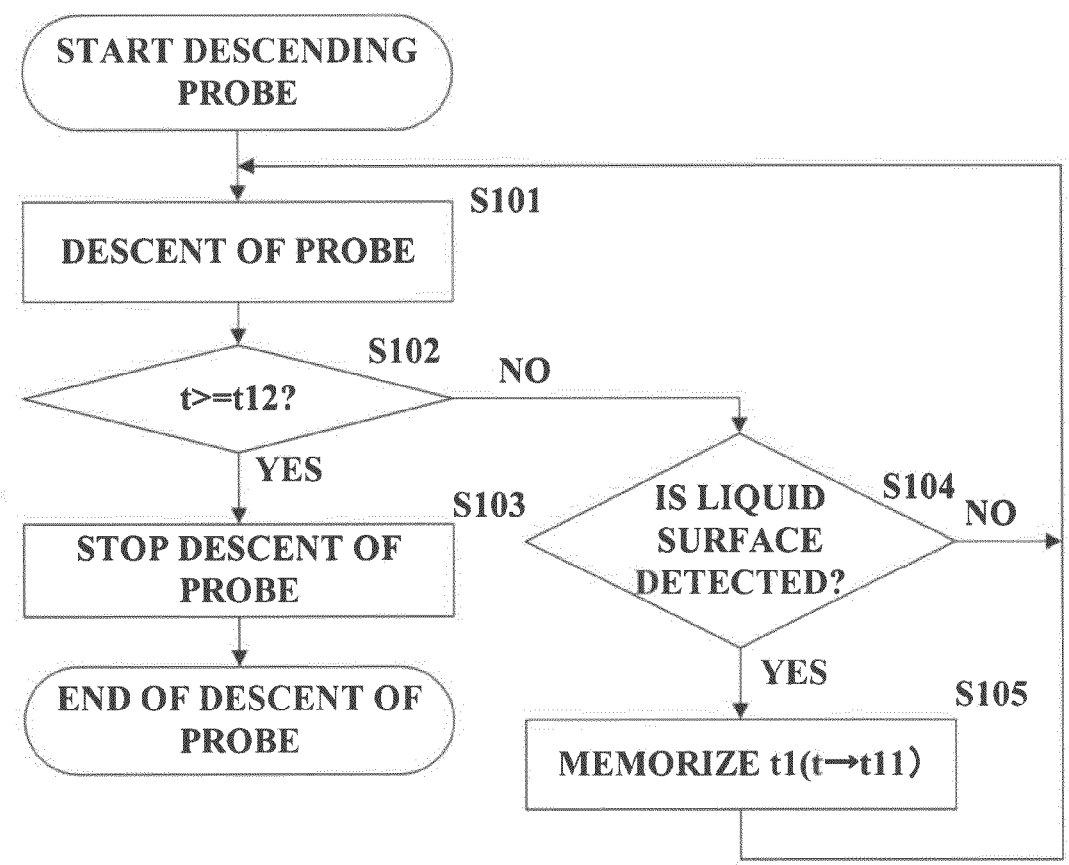
FIG. 9 is a flow chart showing the action of the probe when descending.
Figure 10:
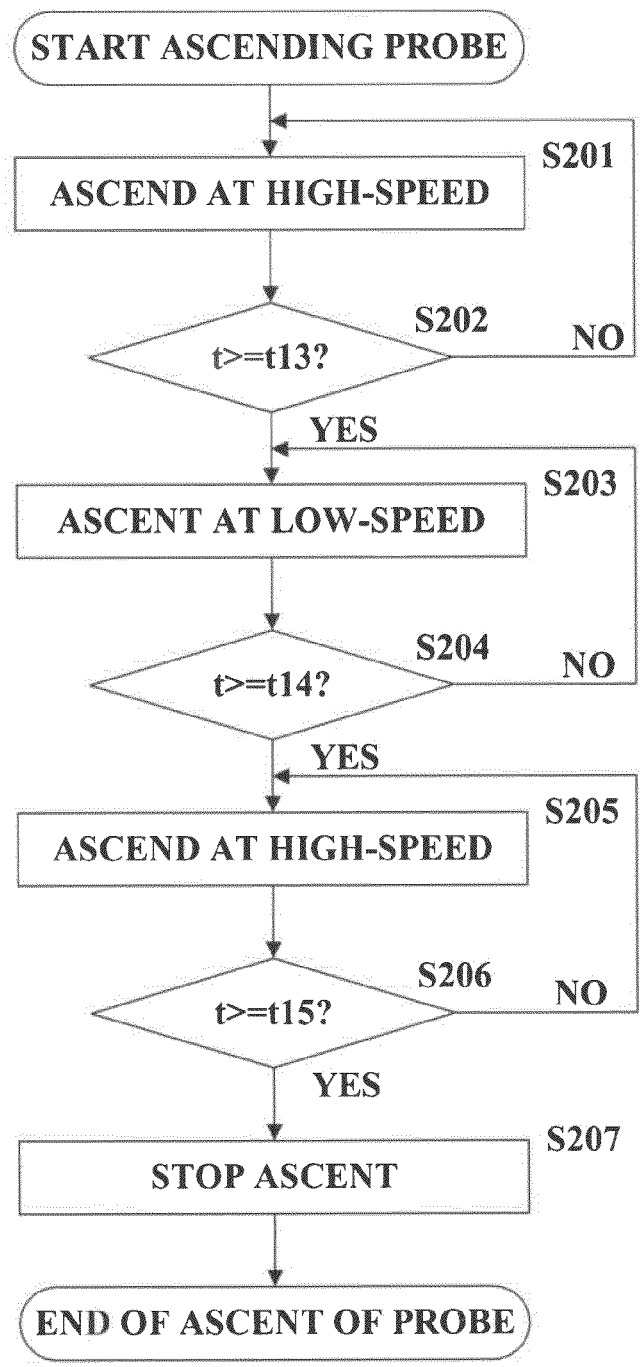
FIG. 10 is a flow chart showing the action of the probe when ascending.

Next, a series of actions of the automated analyzer are described with reference to FIG. 9 and FIG. 10. FIG. 9 is a flow chart showing the respective action of the probe when descending, and FIG. 10 is a flow chart showing the respective action of the probe when ascending.

(Absorption of the Sample)

The sample-probe driver 105, upon receiving a command from the controller 41, rotates the sample arm 102, and moves the sample probe 103 from the standby position to the position of the sample container 101 (absorption position P1). Subsequently, the sample-probe driver 105 lowers the sample probe 103 (Step S101).

The controller 41 determines whether or not the time taken for the sample probe 103 from the start of descent reached the time required t12 (Step S102).

When the elapsed time from starting lowering the sample probe 103 does not reach the required time t12 (Step S102; No), it is determined whether or not the position of the liquid surface is detected and the detection signals are output by the liquid-surface-position detector 181 (Step S104). If the detection signals are not output (Step S104; No), the sample probe 103 continues descending (Step S101). If the detection signals are detected (Step S104; Yes), the controller 41, upon receiving the detection signals, causes the storage part 42 to store the time required t11 that is the elapsed time from starting descending the sample probe 103 (Step S105).

When the elapsed time from starting lowering the sample probe 103 is equal to or more than the required time t12 (Step S102; Yes), the controller 41 completes providing the pulse number n1 to the vertical-movement stepping motor 122A. Based on that, the probe 103 is stopped from descending (Step S103). Next, the solenoid valve that receives a command from the controller 41 operates and causes the sample probe 103 to absorb the sample inside the predefined sample container 101. Therefore, the sample probe 103 is filled with the sample.

(Discharge of the Sample)

Upon receiving a command from the controller 41, the solenoid valve closes. The controller 41, by providing the pulse number n2 to the vertical-movement stepping motor 122A, raises the sample probe 103 at the high speed v2 (Step S201). When the elapsed time from starting raising the sample probe 103 does not reach the required time t13 (Step S202; No), the controller 41 continues raising the sample probe 103 at the high speed v2 (Step S201).

When the elapsed time from starting raising the sample probe 103 reaches the required time t13 (Step S202; Yes), the controller 41, by providing the pulse number n3 to the vertical-movement stepping motor 122A, raises the sample probe 103 at the low speed v3 (Step S203). When the elapsed time from starting raising the sample probe 103 does not reach the required time t14 (Step S204; No), the controller 41 continues raising the sample probe 103 at the low speed v3 (Step S203).

Next, when the elapsed time from starting raising the sample probe 103 reaches required time t14 (Step S204; Yes), the controller 41, by providing the pulse number n4 to the vertical-movement stepping motor 122A, raises the sample probe 103 at the high speed v4 (Step S205). By raising the sample probe 103 at the low speed v3 between the time required t13 and the time required t14, the liquid (blood plasma) does not become attached to the step part 108 of the sample probe 103 that passes through the position of the liquid surface. When the elapsed time from starting raising the sample probe 103 does not reach the time required t15 (Step S206; No), the controller 41 continues raising the sample probe 103 at the high speed v4 (Step S205).

Next, when the elapsed time from starting raising the sample probe 103 reaches the time required t15 (Step S206; Yes), the controller 41, by completing the provision of the pulse number n4 to the vertical-movement stepping motor 122A, stops raising the sample probe 103 (Step S207). With regard to raising the sample probe 103, when causing the step part 108 to pass through the position of the liquid surface, because the ascending speed of the sample probe 103 is set to be at the low speed v3, and others are set to be at the high speed v2, v4, it is possible to maintain the efficiency of the automatic analysis.

Next, the controller 41 rotates the sample arm 102, and moves the sample probe 103 from the position of the sample container 101 (absorption position P1) to the position of the reaction container 301 (discharge position P2). Subsequently, the controller 41 lowers the sample probe 103 by controlling the sample-probe driver 105. Upon receiving a command from the controller 41, the solenoid valve operates and discharges the sample from the sample probe 103 to the predefined reaction container 301.

(Cleaning of the Sample Probe, Moving to the Standby Position)

Next, upon receiving a command from the controller 41, the solenoid valve closes. The controller 41 raises the sample probe 103 by controlling the sample-probe driver 105. Furthermore, the controller 41, by rotating the sample arm 102, moves the sample probe 103 from the position of the reaction containers 301 (discharge position P2) to the cleaning position.

Because the action when cleaning the sample probe 103 is basically the same as that when dispensing the sample with the sample probe 103, as described previously, the explanation is omitted. However, when dispensing the sample, as previously described, the controller 41 controls the vertical-movement stepping motor 122A, based on the control information 421; on the other hand, when cleaning the sample probe 103, it is different in that the controller 41 controls based on the control information 422.

Even for the cleaning of the sample probe 103, when causing the step part 108 to pass through the liquid surface of the cleaning water, because the sample probe 103 is raised at the low speed, it is possible to cause the cleaning water to be less likely to be attached to the step part 108. Based on that, it is not necessary to provide the special means for removing the cleaning water from the step part 108 to the cleaning tank 701, and it is not required to make the cleaning tank 701 complex.

Next, after completing cleaning the sample probe 103, the sample-probe driver 105 moves the sample probe 103 to the standby position.

As above, the structure for controlling the action of the sample probe 103 and a series of actions of the sample probe 103 have been described. Next, the structure of the first and the second reagent storage 200 and the actions of the first and the second reagent storage 200 are described.

The first and the second reagent storage 200 basically have the same structure. The first reagent storage 200 is primarily described below. For the second reagent storage 200, an explanation of the same parts with the first reagent storage 200 is omitted. On the reagent storage 200, the plurality of reagent containers 201 are mounted such that they are placed in a circumferential direction. The reagent-storage driver 204 transports the plurality of reagent containers 201 to an absorption position P3 sequentially by rotating the reagent containers 201 in a circumferential direction. In the reagent containers 201, the reagent that reacts selectively against specific components of the sample is housed.

In the reagent containers 201 of the second reagent storage 200, the reagent that is paired with the reagent that is housed in the reagent containers 201 of the first reagent storage 200 is housed.

At the tip part of the reagent arm 202, the reagent probe 203 is provided. The reagent probe 203 is formed in an axial-shape, as is the case with the sample probe 103, and has a lower shaft in which the outer diameter is formed so as to be small, an upper shaft in which the outer diameter is formed so as to be large, and a step part that is formed such that the size of the outer diameter changes between the lower shaft and the upper shaft. The reagent probe 203 absorbs the reagent from the reagent containers 201 that are transported to the absorption position P3 and discharges the absorbed reagent to the reaction containers 301 that is transported to a discharge position P4. The reagent arm 202 rotates the reagent probe 203 between the absorption position P3 and the discharge position P4 so as to reciprocate.

In the reaction storage 300, the plurality of reaction containers 301 are housed. The reaction storage 300 has a reaction line 330 and the reaction-storage driver 304. On the reaction line 330, the plurality of reaction containers 301 are mounted in a state in which they are placed in a circumferential direction. The reaction-storage driver 304 transports the plurality of reaction containers 301 to the discharge position P4 sequentially by rotating the reaction line 330 in a circumferential direction.

A series of the actions of the reagent probe 203 that are performed in the above structure are described.
(Absorption of Reagent)

The reagent-probe driver 205, upon receiving a command from the controller 41, rotates the reagent arm 202 and moves the reagent probe 203 from the standby position to the absorption position P3. Furthermore, the reagent-probe driver 205 lowers the reagent probe 203. Upon receiving a command from the controller 41, the solenoid valve operates and causes the reagent probe 203 to absorb the reagent from the predefined reagent container 201.

(Discharge of Reagent)

Upon receiving a command from the controller 41, the solenoid valve operates. The reagent-probe driver 205 moves the reagent probe 203 from the absorption position P3 to the discharge position P4 by raising the reagent probe 203 and rotating the reagent arm 202. Subsequently, the reagent-probe driver 205 lowers the reagent probe 203. Upon receiving a command from the controller 41, the solenoid valve operates and causes to discharge the sample from the reagent probe 203 to the predefined reaction container 301.

(Cleaning of the Reagent Probe, Moving to the Standby Position)

Next, upon receiving a command from the controller 41, the solenoid valve closes. The reagent-probe driver 205 moves the reagent probe 203 from the discharge position P4 to the cleaning position by raising the reagent probe 203 and rotating the reagent arm 202. After completing washing the reagent probe 203, the reagent-probe driver 205 moves the reagent probe 203 to the standby position.

(Stirring and Measuring)

Based on the above, the reaction containers 301 to which the sample and the reagent are dispensed are moved toward a photometic unit 190 by the reaction-storage driver 304. Meanwhile, the sample and the reagent inside the reaction containers 301 are stirred with a stirring bar (omitted in the figures). The photometic unit 190 irradiates light on the reaction containers 301 that have been stirred, and measures the absorbance for predefined wavelength from the permeated light.

The above embodiment shows the controller 41 that switches the ascending speed of the sample probe 103 between the low speed and the high speed, by providing the predefined pulse number to the vertical-movement stepping motor 122A. That is, immediately before the step part of sample probe 103 passes through the position of the liquid surface, the ascending speed of the sample probe 103 is switched from the high speed to the low speed, and furthermore, immediately after the step part pass through the position of the liquid surface, the ascending speed of the sample probe 103 is switched from the low speed to the high speed. However, the switching of the ascending speed is not limited to the sample probe 103. For the reagent with which the vicinity of the liquid surface deteriorates, the reagent can be considered to be absorbed from the middle or the lower section inside the reagent. For example, when the reagent probe 203 for dispensing the reagent has a step part and when dispensing the reagent by positioning this step part below the liquid surface of the reagent, the controller 41, as is the case with the sample probe 103, can switch the ascending speed of the reagent probe 203 between the low speed and the high speed by providing the predefined pulse number to a vertical-movement stepping motor of the reagent-probe driver 205 (omitted in the figures). That is, immediately before the step part of the reagent probe 203 passes through the position of the liquid surface, the ascending speed of the reagent probe 203 may be switched from the high speed to the low speed, and furthermore, immediately after the step part passes through the position of the liquid surface, the ascending speed of the reagent probe 203 may be switched from the low speed to the high speed.

Moreover, in the above embodiment, the controller 41, upon receiving the detection signals from the liquid-surface-position detector 181, caused the storage part 42 to store the time required from starting descending the sample probe 103 until it reaches the liquid surface of the liquid; however, the controller 41 may be configured to cause storage part 42 to store the time required, upon receiving an input of the time required by an operation from the operation part 61.

Furthermore, in the above embodiment, for the ascending period of the probe, from immediately before the step part passes through the position of the liquid surface until the step part passes through the position of the liquid surface is defined to be the low speed period, and other period is defined to be the high speed period; however, they are not limited to these. As another embodiment, for example, from immediately before the step part passes through the position of the liquid surface up to the predefined position may be defined to be the low speed period and other period may be defined to be the high speed period. Moreover, from the operating position until the step part that has started ascending passes through the position of the liquid surface may be defined to be the low speed period, and other period may be defined to be the high speed period. Based on that, without substantially lowering the efficiency of a series of actions of the automatic analysis, it is possible to cause the cleaning solution to be less likely to be attached to the step part. Moreover, according to another embodiment described above, it is not necessary for the speed during the low speed period to be at a fixed speed, and the speed may change within an allowable range in a series of actions.

Furthermore, according to the above embodiment, the control information for controlling the sample-probe driver 105 and the reagent-probe driver 205 is the control information that is obtained by detection of the position of the liquid surface, or the control information that is previously defined by an input from the operation part 61; however, the sample-probe driver 105 and the reagent-probe driver 205 may be controlled by the predefined default value.

Second Embodiment

The above automated analyzer according to the first embodiment, when raising the sample probe 103 from inside the sample container 101 in order to dispense the sample, the controller 41 controls the sample-probe driver 105 so as to raise the sample probe 103 at low speed in the section from immediately before the step part 108 of the sample probe 103 passes through the liquid surface until immediately after it passes through, such that the liquid is not attached to the step part 108.

However, there are cases in which not only is the liquid attached to the step part 108 of the sample probe 103, but also it is attached to the lower end 109 of the sample probe 103. One example of the structure for not causing the liquid to be attached to the step part 108 and the lower end 109 is described.

The sample-probe driver 105, upon receiving a control from the controller 41, in at least specific sections for the comparison section, may raise the sample probe 103 at the low speed. Here, the comparison section includes the section from the operating position of the sample probe 103 (shown in a phase (a3) in FIG. 11) until immediately before the step part 108 reaches the position of the liquid surface (shown in a phase (b1) in FIG. 11), and the section from immediately after the lower end 109 of the sample probe 103 passes through the position of the liquid surface (shown in a phase (b4) in FIG. 11) to the predefined position (shown in a phase (a1) in FIG. 11). The specific sections include the section from immediately before the step part 108 reaches the position of the liquid surface (shown in a phase (b1) in FIG. 11) until the step part 108 passes through the position of the liquid surface (shown in a phase (b2) in FIG. 11), and the section from immediately before the lower end 109 of the sample probe 103 reaches the position of the liquid surface (shown in a phase (b3) in FIG. 11) until the lower end 109 passes through the position of the liquid surface (shown in a phase (b4) in FIG. 11).

Figure 11:
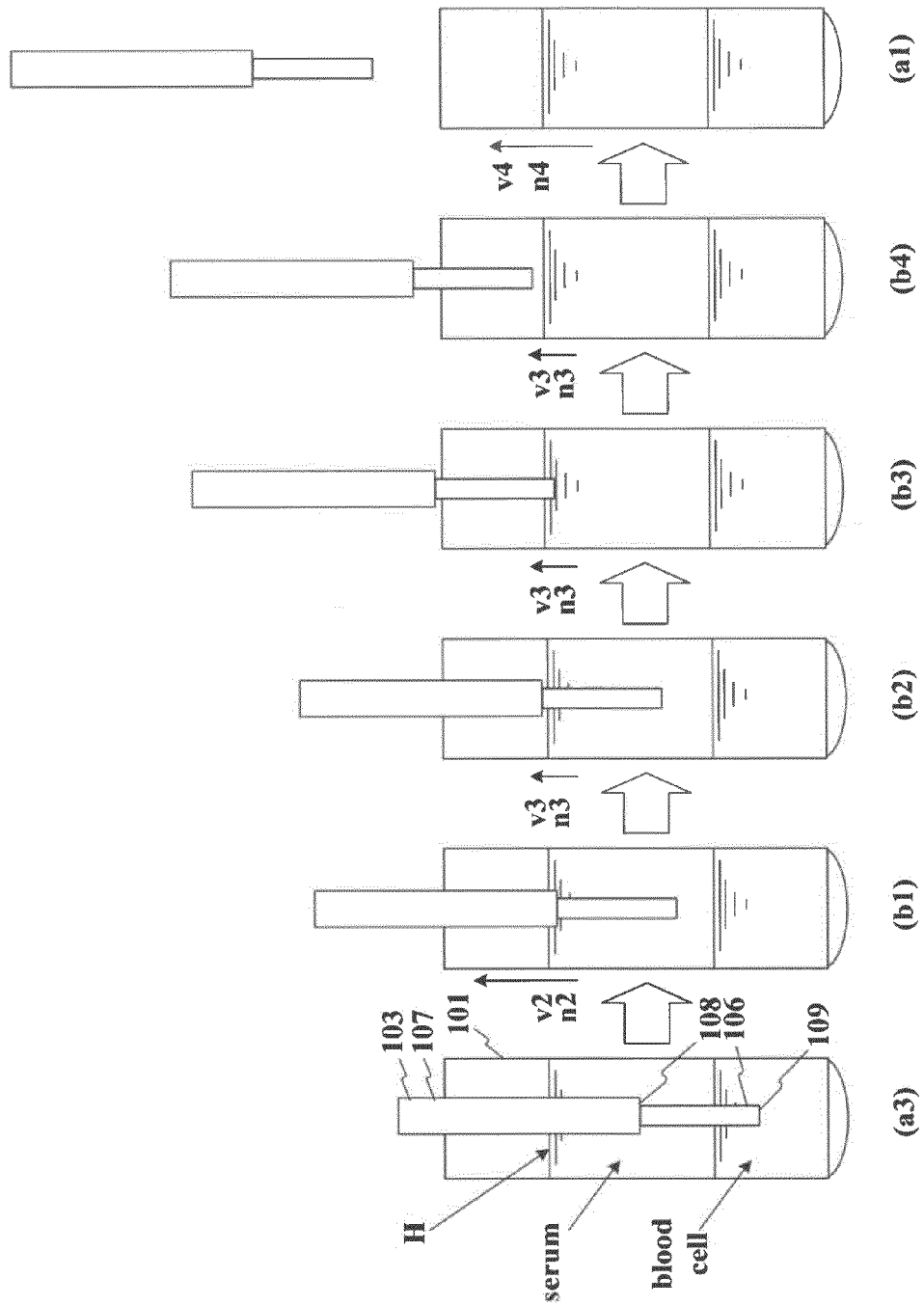
FIG. 11 is a diagram showing the moving speed of a probe of an automated analyzer according to the second embodiment when ascending.
Figure 12:
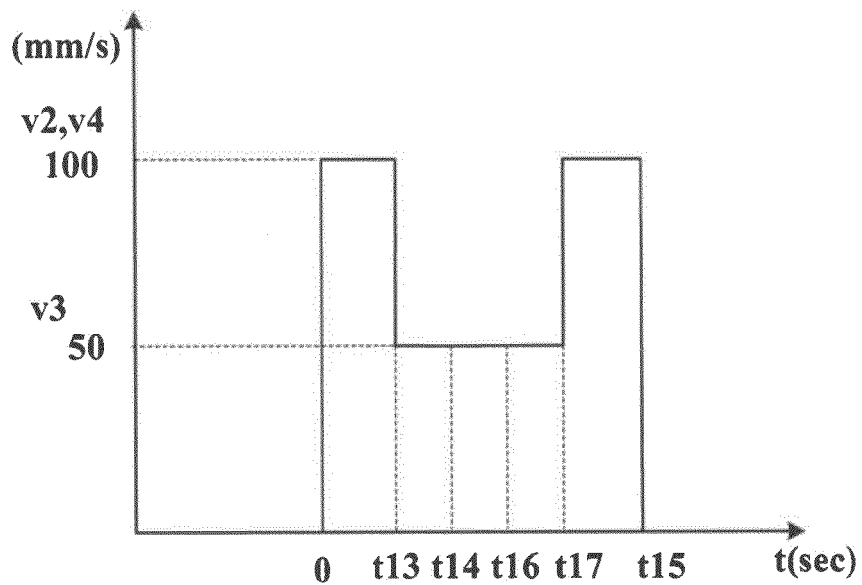
FIG. 12 is a velocity diagram of the probe when ascending.

As an embodiment for controlling the sample-probe driver 105 as above, the structure of the automated analyzer according to the second embodiment is described with reference to FIG. 11 and FIG. 12. FIG. 11 is a diagram showing the moving speed of the sample probe 103 when ascending. FIG. 12 is a velocity diagram of the probe when ascending. With regard to the second embodiment, the structure for controlling the sample-probe driver 105 such that the liquid is not attached to the step part 108 and the lower end 109 of the sample probe 103 is described.

In the first embodiment, although it is switched from the low speed to the high speed immediately after the step part 108 of the sample probe 103 passed through the liquid surface (shown in a phase (b2) in FIG. 6), in the second embodiment, it is switched from the low speed to the high speed immediately after the lower end 109 passed through the liquid surface (shown in a phase (b4) in FIG. 11 and in FIG. 12 as t17). Therefore, in the section from immediately before the step part 108 of the sample probe 103 passes through the liquid surface (shown in a phase (b1) in FIG. 11 and in FIG. 12 as t13) until immediately after the lower end 109 of the sample probe 103 passes through the liquid surface (shown in a phase (b4) in FIG. 11 and in FIG. 12 as t17), the sample-probe driver 105 is controlled so as to raise the sample probe 103 at the low speed.

Third Embodiment

Figure 14:
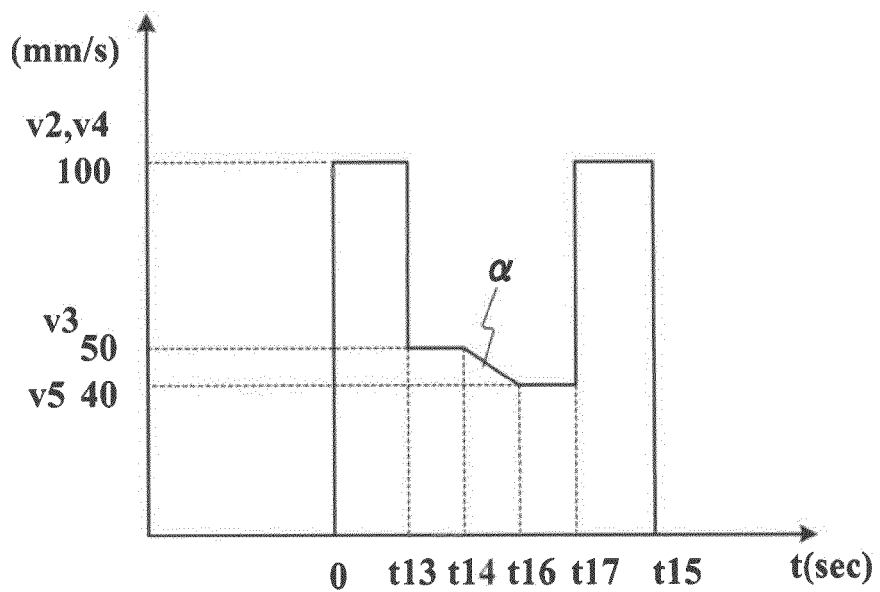
FIG. 14 is a velocity diagram of the probe when ascending.
Figure 13:
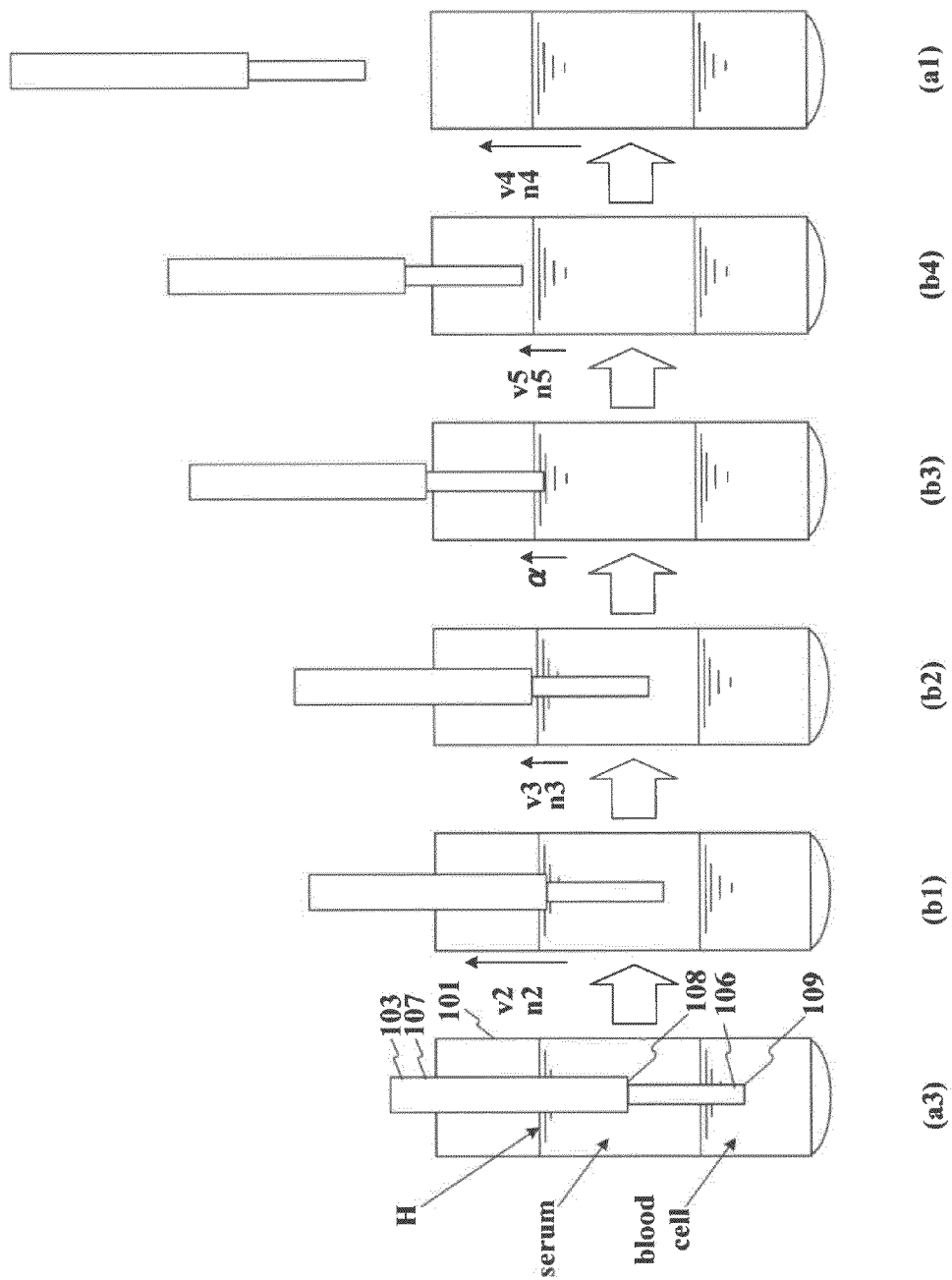
FIG. 13 is a diagram showing the moving speed of the probe of an automated analyzer according to the third embodiment when ascending.

As another embodiment for controlling the sample-probe driver 105, the structure of the automated analyzer according to the third embodiment is described with reference to FIG. 13 through FIG. 16. FIG. 13 is a diagram showing the moving speed of the probe when ascending. FIG. 14 is a velocity diagram of the probe when ascending.

Figure 15:
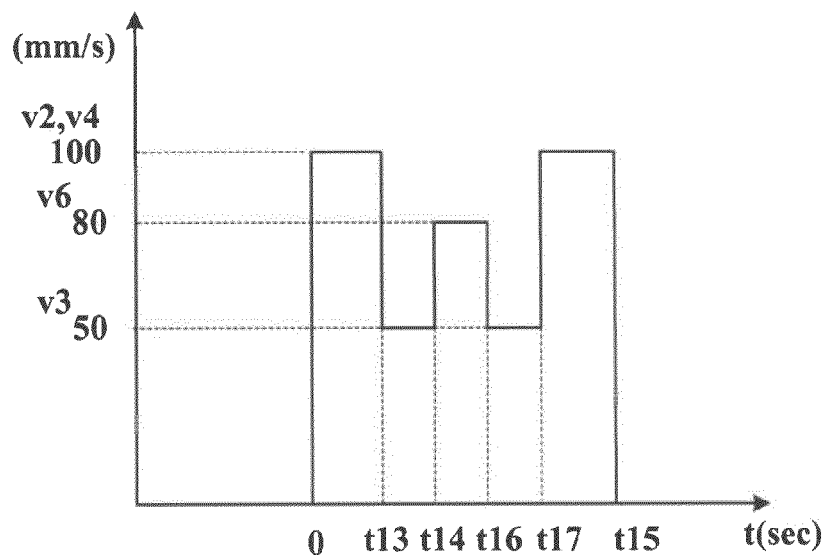
FIG. 15 is a velocity diagram of the probe according to a modified example when ascending.
Figure 16:
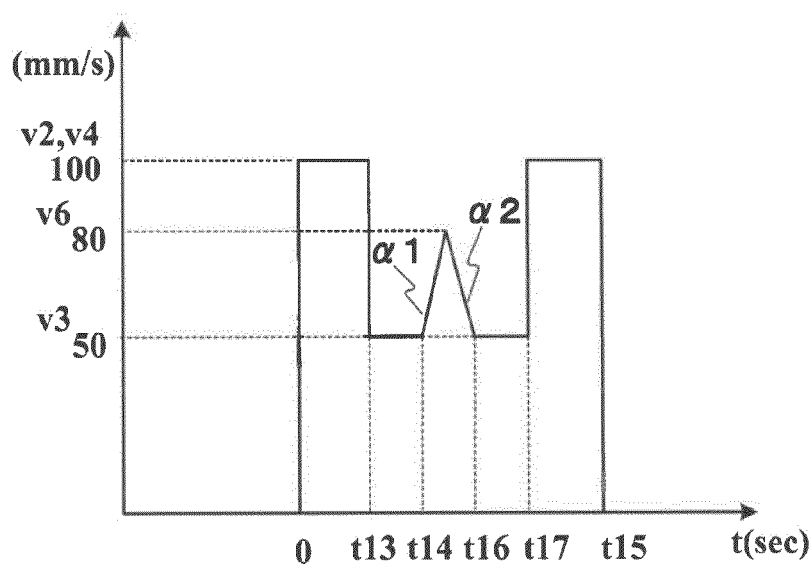
FIG. 16 is a velocity diagram of the probe according to another modified example when ascending.

FIG. 15 is a velocity diagram of the probe according to a modified example when ascending. FIG. 16 is a velocity diagram of the probe according to another modified example when ascending.

With regard to the third embodiment, the structure for controlling the sample-probe driver 105 such that the liquid is not attached to the step part 108 and the lower end 109 of the sample probe 103 is also described.

In the second embodiment, once the sample-probe driver 105 receives a control from the controller 41, for the section from immediately before the step part 108 of the sample probe 103 passed through the liquid surface until immediately after the lower end 109 of the sample probe 103 passed through the liquid surface, the sample probe 103 is raised at the low speed. On the other hand, in the third embodiment, when the sample-probe driver 105 raises the sample probe 103, the sample probe 103 is slowed down. For example, when the amount of the liquid that is attached to the lower end 109 of the sample probe 103 exceeds the amount of the liquid that is attached to the step part 108, as the decelerating section in which the sample probe 103 is decelerated, the section from immediately after the step part 108 of the sample probe 103 passes through the liquid surface (shown in a phase (b2) in FIG. 13 and in FIG. 14 as t14) until immediately before the lower end 109 of the sample probe 103 passes through the liquid surface (shown in a phase (b3) in FIG. 13 and in FIG. 14 as t16) is set. FIG. 14 shows the deceleration α in the deceleration section from the t14 to t16.

Moreover, as is the case with the second embodiment, when the sample probe 103 is raised at low speed in dispensing the sample, the operation efficiency of the sample probe 103 may decrease.

Therefore, in the section that is not required to be raised at the low speed, the sample-probe driver 105 is controlled so as to raise the sample probe 103 at the high speed. For example, by controlling the sample-probe driver 105, a third section in which the sample probe 103 is raised at the high speed is provided between a first section and a second section below. The first section is a section from immediately before the step part 108 reaches the position of the liquid surface until the step part 108 passes through the position of the liquid surface (shown in FIGS. 15 as t13-t14). The second section is a section from immediately before the lower end 109 of the sample probe 103 reaches the position of the liquid surface until the lower end 109 passes through the position of the liquid surface (shown in FIG. 15 as t16~t17). The third section is a section in which the moving speed is at 80 (mm/s) (shown in FIG. 15 as t14-t16).

Moreover, this high speed (80 (mm/s)) may be the speed exceeding the low speed (for example, 50 (mm/s) (the speed v3 shown in FIG. 15), and for example, it may exceed 100 (mm/s) (the speed v2 and v4 shown in FIG. 15).

Moreover, there are cases in which the third section between the first section and the second section is short, and in which it is difficult to provide a section with a fixed moving speed (for example, 80 (mm/s)) within the third section. Therefore, in the third section (shown in FIG. 16 as t14-t16), an acceleration section and a deceleration section are provided. FIG. 16 shows examples of the acceleration α1 in the acceleration section and the deceleration α2 in the deceleration section.

Moreover, in the second embodiment and the third embodiment, when the amount of the liquid that is attached to the step part 108 is extremely small and when it does not cause measurement error, it may control the sample-probe driver 105 such that the liquid is not attached only to the lower end 109 of the sample probe 103. In order not to cause the liquid to be attached to the step part 108 of the sample probe 103, it may not have to control the sample-probe driver 105 so as to raise the sample probe 103 at the low speed.

Fourth Embodiment

Figure 17:
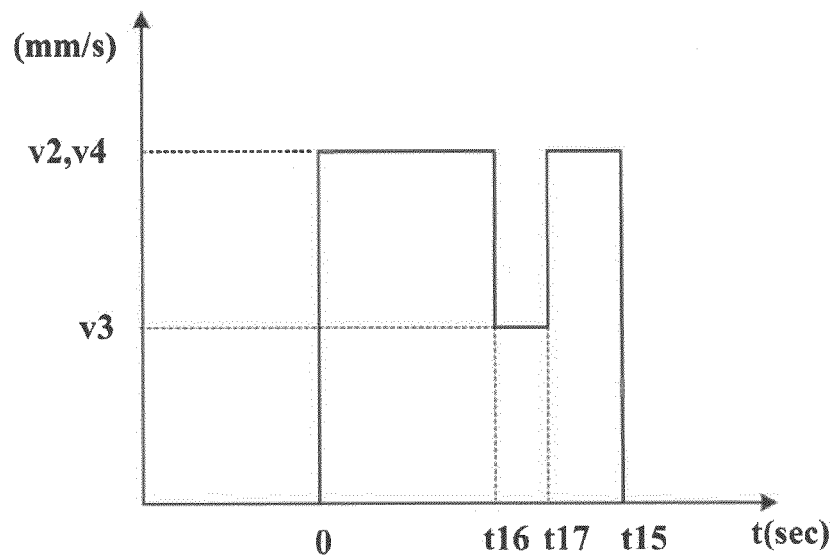
FIG. 17 is a velocity diagram of the probe of an automated analyzer according to the fourth embodiment when ascending.

Next, the automated analyzer according to the fourth embodiment is described with reference to FIG. 17 through FIG. 19.

The automated analyzer according to the fourth embodiment has a structure so as to control the sample-probe driver 105 such that the liquid is not attached only to the lower end 109 of the sample probe 103. The structure so as to control the sample-probe driver 105 according to the fourth embodiment is basically the same as the structure so as to control the sample-probe driver 105 such that the liquid is not attached to the step part 108 of the sample probe 103 in the first embodiment. As a difference, the timing for switching the ascending speed of the sample probe 103 is different.

In the first embodiment, the ascending speed of the sample probe 103 is switched at the timing shown in FIG. 7B. In contrast, in the fourth embodiment, for example, the ascending speed is switched at the timing shown in FIG. 17. That is, from the operating position until immediately before the lower end 109 reaches the position of the liquid surface (shown in FIG. 17 as t16), the sample probe 103 is raised at the high speed v2. Subsequently, the sample probe 103 is raised at the lower speed v3 than the high speed v2 until the lower end 109 passes through the position of the liquid surface (shown in FIG. 17 as t17). The sample probe 103 is raised at the higher speed v4 than the lower speed v3 from immediately after the lower end 109 passes through the position of the liquid surface (shown in FIG. 17 as t17) up to the pre-defined position (shown in FIG. 17 as t15).

Figure 18:
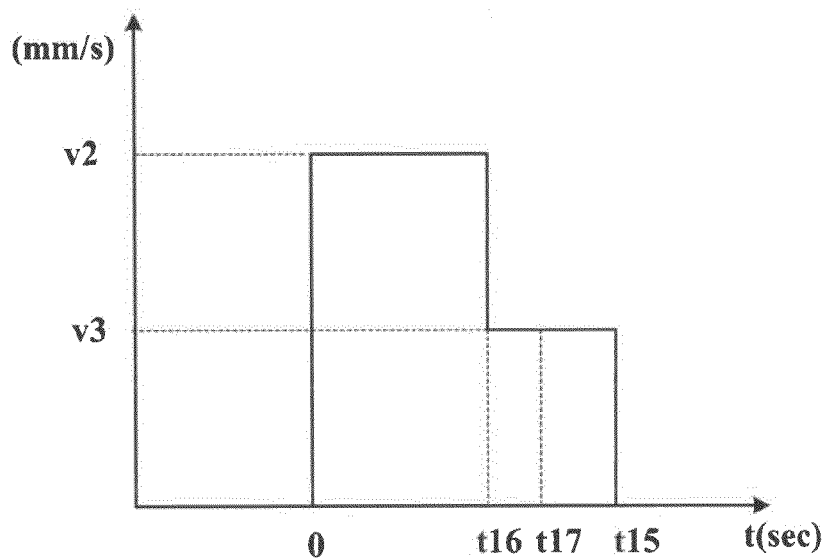
FIG. 18 is a velocity diagram of the probe according to another example when ascending.

Moreover, as another example of the fourth embodiment, as shown in FIG. 18, the sample probe 103 is raised at the high speed v2 from the operating position until immediately before the lower end 109 reaches the position of the liquid surface (shown in FIG. 18 as t16). Subsequently, the sample probe 103 is raised at the lower speed v3 than the high speed v2 up to the predefined position (shown in FIG. 18 as t15).

Figure 19:
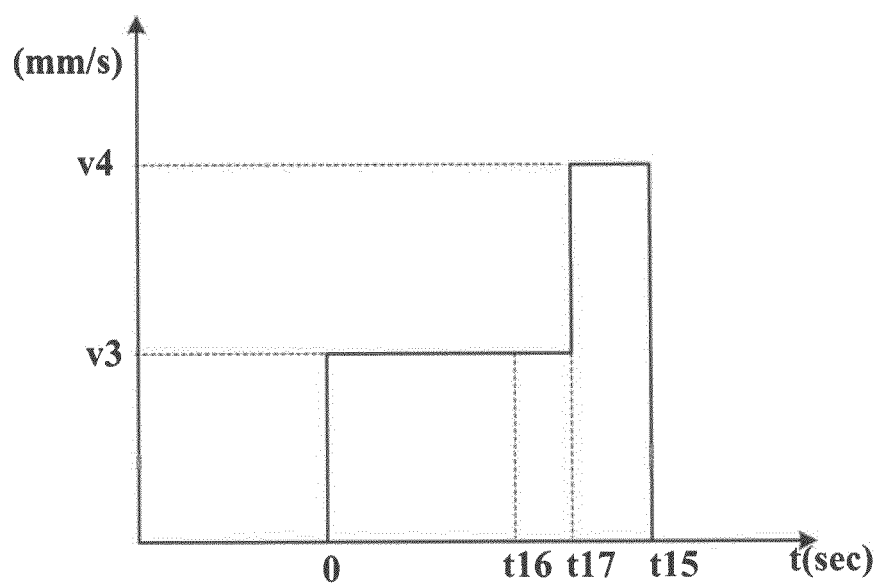
FIG. 19 is a velocity diagram of the probe according to another example when ascending.
Figure 20:
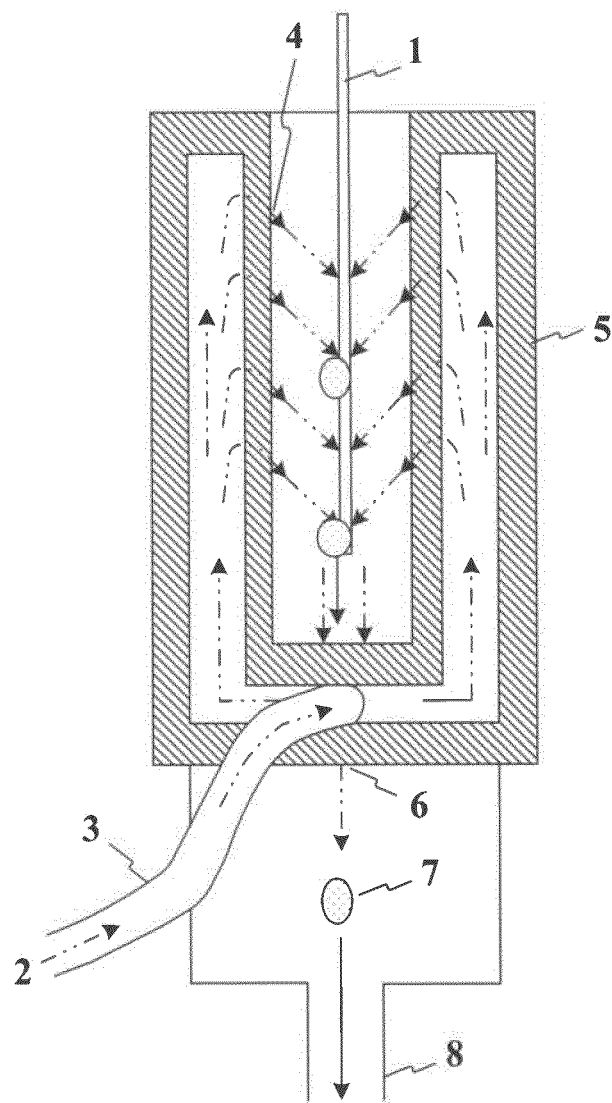
FIG. 20 is a diagram showing an conventional art that sprays gas to a probe from both sides.

Furthermore, as another example of the fourth embodiment, as shown in FIG. 19, the sample probe 103 is raised at the lower speed v3 than the high speed v4 from the operating position until the lower end 109 passes through the position of the liquid surface (shown in FIG. 19 as t17). From immediately after the lower end 109 passes through the position of the liquid surface (shown in FIG. 19 as t17) up to the predefined position (shown in FIG. 19 as t15), the sample probe 103 is raised at the higher speed v4 than the low speed v3.

In the above fourth embodiment, although the sample-probe driver 105 has been shown as the control subject, the control subject may be the reagent probe 203. As is the case with the first to the third embodiments, by controlling the reagent-probe driver 205, the ascending speed of the reagent probe 203 may be switched.

[Effect]

Next, the effect that is achieved by the structure of the automated analyzer according to the various embodiments described above is described.

According to the automated analyzer in these embodiments, without complicating the structure of the cleaning tank, it is possible to cause the liquid to be less likely to be attached to the step part of the probe in a relatively short time.

Moreover, according to the automated analyzer in one embodiment, without reducing the efficiency of a series of actions of the automatic analysis, it is possible to cause the liquid to be less likely to be attached to the step part, by raising the probe at a low speed when the step part passes through the position of the liquid surface, based on the position of the liquid surface.

Moreover, according to the automated analyzer in another embodiment, it is possible to cause the liquid to be less likely to be attached to the step part by raising the probe at a low speed from immediately before the step part passes through the position of the liquid surface up to the predefined position so as not to substantially reduce the efficiency of a series of actions of the automatic analysis.

Furthermore, according to the automated analyzer in another embodiment, it is possible to cause the liquid to be less likely to be attached to the step part by raising the probe at a low speed from the operating position until the step part passes through the position of the liquid surface so as not to substantially reduce the efficiency of a series of actions of the automatic analysis.

Furthermore, according to the automated analyzer in another embodiment, it is possible to cause the liquid to be less likely to be attached to the step part and the lower end by raising the probe at a low speed so as not to substantially reduce the efficiency of a series of actions of the automatic analysis, with respect to at least the section in which the step part passes through the position of the liquid surface, and the section in which the lower end of the probe passes through the position of the liquid surface.

Furthermore, according to the automated analyzer in another embodiment, without reducing the efficiency of a series of actions of the automatic analysis, it is possible to cause the liquid to be less likely to be attached to the lower end, by raising the probe at a low speed, based on the position of the liquid surface, when the lower end passes through the position of the liquid surface.

Furthermore, according to the automated analyzer in another embodiment, it is possible to cause the liquid to be less likely to be attached to the lower end by raising the probe at a low speed from immediately before the lower end passes through the position of the liquid surface up to the predefined position so as not to substantially reduce the efficiency of a series of actions of the automatic analysis.

Furthermore, according to the automated analyzer in another embodiment, it is possible to cause the liquid to be less likely to be attached to the lower end by raising the probe at a low speed from the operating position until the lower end of the probe passes through the position of the liquid surface so as not to substantially reduce the efficiency of a series of actions of the automatic analysis.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of embodiments described herein may be made without departing from the spirit of the inventions. The accompanying claims and their equivalents are intended to cover such forms or modifications as would fall within the scope and spirit of the inventions.

What is claimed is:

1. An automated analyzer that includes an axial probe configured to move between below the liquid surface of any liquid among a sample, reagent, and cleaning water and above said liquid surface, dispense said sample and said reagent into a reaction container, and be cleaned with said cleaning water, and that analyzes components of a reaction solution generated from said dispensed sample and reagent, wherein:

said probe includes an upper shaft having an outer diameter, a lower shaft having an outer diameter smaller than the outer diameter of the upper shaft and a step part formed between the upper shaft and lower shaft, the step part having a surface disposed perpendicular to the axial direction of the probe;

said automated analyzer includes, said liquid in a container, a descending controller configured to lower said probe into said container, an ascending controller configured to raise said probe out of said container, and a liquid surface position detector configured to detect the actual position of the liquid surface of the liquid in said container;

said descending controller configured to lower said probe from a predefined position that positions said step part above the actual position of the liquid surface of said liquid detected by the liquid position detector to an operating position for performing absorption of said liquid or washing with said cleaning water by positioning said step part below the actual position of said liquid surface; and said ascending controller configured to raise said probe at a first speed from said operating position until immediately before said step part reaches the actual position of said liquid surface, subsequently raise said probe at a second speed that is lower than said first speed until said step part passes through the actual position of said liquid surface, and raise said probe at a higher speed than said second speed from immediately after said step part passes through the actual position of said liquid surface up to said predefined position.

2. The automated analyzer according to claim 1, wherein said second speed is equal to or less than 50 mm/sec.

3. The automated analyzer according to claim 1, having an operation part configured to adjust said second speed within a predefined range.

* * * * *